(12) United States Patent
Berger et al.

(10) Patent No.: US 11,160,596 B2
(45) Date of Patent: *Nov. 2, 2021

(54) CATHETER WITH JET IMPINGEMENT COOLED THERMOELECTRIC MODULE

(71) Applicant: Berger Thermal Research Ltd., Tel Aviv (IL)

(72) Inventors: Abraham Berger, Givataim (IL); Avri Hazan, Givataim (IL)

(73) Assignee: Berger Thermal Research Ltd., Tel Aviv (IL)

( * ) Notice: Subject to any disclaimer, the term of this patent is extended or adjusted under 35 U.S.C. 154(b) by 1018 days.

This patent is subject to a terminal disclaimer.

(21) Appl. No.: 15/817,808

(22) Filed: Nov. 20, 2017

(65) Prior Publication Data

US 2018/0071007 A1 Mar. 15, 2018

Related U.S. Application Data

(63) Continuation of application No. 14/511,989, filed on Oct. 10, 2014, now Pat. No. 9,820,795, which is a
(Continued)

(30) Foreign Application Priority Data

Apr. 30, 2012 (IL) .......................................... 219477

(51) Int. Cl.
*A61B 18/02* (2006.01)
*A61B 18/14* (2006.01)
(Continued)

(52) U.S. Cl.
CPC .......... *A61B 18/02* (2013.01); *A61B 18/1492* (2013.01); *A61M 5/007* (2013.01);
(Continued)

(58) Field of Classification Search
CPC .. A61B 2018/0243; A61B 2018/00029; A61B 2218/002; A61B 2018/0237; A61B 2018/00047; A61F 2007/0075
See application file for complete search history.

(56) References Cited

U.S. PATENT DOCUMENTS 4,860,744 A 8/1989 Johnson et al.
5,139,496 A 8/1992 Hed
(Continued)

FOREIGN PATENT DOCUMENTS

FR 2613611 A1 10/1988
JP 2005137792 A 6/2005
(Continued)

OTHER PUBLICATIONS

X. Liu et al., Convective Heat Transfer by Impingement of Circular Liquid Jets, Journal of Heat Transfer, Aug. 1991, vol. 113/571.
(Continued)

*Primary Examiner* — Jaymi E Della
(74) *Attorney, Agent, or Firm* — Novick, Kim & Lee, PLLC; Harold L. Novick; Hyun Woo Shin

(57) ABSTRACT

Cryocatheter including an elongated flexible catheter member having a short rigid catheter tip for introduction into a therapy site and a heat exchange arrangement for freezing the catheter tip to a cryo-temperature from between about −15° C. to about −30° C. for freezing human tissue at the therapy site. Cerebral medical procedures include inter alia employing a local ice ball for sealing a bleeding rupture in an arterial wall in the case of a stroke hemorrhage, employing a local ice ball for mapping electrical disorder foci in a brain, for example, epileptic foci, and the like.

7 Claims, 34 Drawing Sheets

Related U.S. Application Data continuation-in-part of application No. PCT/IL2013/050363, filed on Apr. 30, 2013.

(60) Provisional application No. 61/890,078, filed on Oct. 11, 2013.

(51) Int. Cl.
*A61M 5/00* (2006.01)
*A61M 5/14* (2006.01)
*A61B 18/00* (2006.01)
*A61F 7/00* (2006.01)

(52) U.S. Cl.
CPC ..... *A61M 5/14* (2013.01); *A61B 2018/00023* (2013.01); *A61B 2018/00029* (2013.01); *A61B 2018/00041* (2013.01); *A61B 2018/00047* (2013.01); *A61B 2018/00095* (2013.01); *A61B 2018/00404* (2013.01); *A61B 2018/00577* (2013.01); *A61B 2018/00714* (2013.01); *A61B 2018/00839* (2013.01); *A61B 2018/00863* (2013.01); *A61B 2018/025* (2013.01); *A61B 2018/0212* (2013.01); *A61B 2018/0237* (2013.01); *A61B 2018/0243* (2013.01); *A61B 2018/0281* (2013.01); *A61B 2218/002* (2013.01); *A61F 2007/0075* (2013.01)

(56) References Cited

U.S. PATENT DOCUMENTS

| | | | | |
|---|---|---|---|---|
| 5,733,280 | A | * | 3/1998 | Avitall ................. A61B 18/02 606/20 |
| 5,807,391 | A | | 9/1998 | Wijkamp |
| 6,017,337 | A | * | 1/2000 | Pira ....................... A61B 18/02 601/15 |
| 6,096,032 | A | | 8/2000 | Rowland |
| 7,238,184 | B2 | | 7/2007 | Megerman et al. |
| 8,083,732 | B2 | | 12/2011 | Arless et al. |
| 2004/0167467 | A1 | | 8/2004 | Harrison et al. |
| 2004/0267338 | A1 | | 12/2004 | Harrison |
| 2006/0025840 | A1 | | 2/2006 | Willard |
| 2007/0225781 | A1 | | 9/2007 | Saadat et al. |
| 2010/0057072 | A1 | | 3/2010 | Roman et al. |
| 2011/0196359 | A1 | | 8/2011 | Arless et al. |

FOREIGN PATENT DOCUMENTS

| | | | |
|---|---|---|---|
| JP | 2006130024 A | * | 5/2006 |
| JP | 2006130024 A | | 5/2006 |
| WO | 9419833 A1 | | 9/1994 |
| WO | 98/06339 A1 | | 2/1998 |
| WO | 01/67975 A2 | | 9/2001 |
| WO | 02080766 A2 | | 10/2002 |
| WO | 2010121739 A1 | | 10/2010 |

OTHER PUBLICATIONS

M. R. Holman et al., Design and development of a new cryosurgical instrument utilizing the Peltier thermoelectric affect, Journal of Medical Engineering & Technology, May-Aug. 1997, pp. 106-110, vol. 21, No. 3-4.

Shigenao Maruyama et al., The Flexible Cryoprobe Using Peltier Effect for Heat Transfer Control, Journal of Biomechanical Science and Engineering, 2008, pp. 138-150, vol. 3, No. 2.

B. Elison et al., Local heat transfer to impinging liquid jets in the initially laminar, transitional, and turbulent regimes, Int. J. Heat Mass Transfer, 1994, vol. 37. No 8, pp. 1207-1216.

Partial Supplementary European Search Report for corresponding European patent application No. 13785143.2 (PCT/IL2013/050363) dated Nov. 3, 2016.

* cited by examiner

CATHETER WITH JET IMPINGEMENT COOLED THERMOELECTRIC MODULE

CROSS-REFERENCE TO RELATED APPLICATIONS

This application is a continuation under 35 USC § 120 of U.S. patent application Ser. No. 14/511,989 filed on Oct. 10, 2014, now U.S. Pat. No. 9,820,795 issued on Nov. 21, 2017, which claims the priority to U.S. Provisional Patent Application No. 61/890,078 filed on Oct. 11, 2013, and is a continuation-in-part of International Patent Application No. PCT/IL2013/050363 filed on Apr. 30, 2013, which claims priority to Israel Patent Application No. 219,477 filed on Apr. 30, 2012, and the entire contents of the aforementioned applications are hereby incorporated by reference.

FIELD OF THE INVENTION

The invention relates to catheters in general and cryocatheters for cryotherapy at a therapy site in particular, and also cerebral medical procedures.

BACKGROUND OF THE INVENTION

The invention is directed toward catheters having an elongated flexible catheter member and a short rigid catheter tip. Catheter members are typically about 0.5 m to 1.5 m long depending on its intended clinical application. Rigid catheter tips are typically about 0.3 cm to 1.5 cm long. The catheter members and the catheter tips have a 1.65 mm to 3.3 mm outside diameter corresponding to French Gauge 5-10. Catheter tips terminate in a leading catheter dome typically formed from bio-compatible materials such as platinum, iridium, and the like. For certain surgical procedures, catheter tips are intended to be introduced into a human lumen via an externally accessible access port to be steered therealong to a therapy site for therapy thereat before being pulled back along the human lumen to leave therefrom at the access port in a single clinical procedure. In greater particularity, the present invention is directed towards cryocatheters for cryotherapy at a therapy site at cryo-temperatures which in the context of the present invention are sub-zero tip temperatures of −10° C. and colder.

Cryocatheters are presently implemented employing the Joule-Thomson effect, namely, passing a liquid, gas or vapor refrigerant through a pressure line at 70 bar to 150 bar to exit through a restriction at a catheter tip. The restriction causes a phase change from, say, liquid to vapor, to cause a loss of pressure with consequent loss of heat and rapid cooling to freeze a catheter tip to a cryo-temperature. Exemplary prior art patent publications include inter alia U.S. Pat. No. 5,807,391 to Wijkamp entitled CryoAblation Catheter, US Patent Application Publication No. 2011/0196359 entitled Catheter with Cryogenic and Electrical Heating Ablation, PCT International Publication No. WO 2010/121739 entitled Cryosurgical Instrument particularly suitable for transbronchial biopsy, and the like.

Cryocatheters are commercially available from Medtronic CryoCath, Inc. www.cryocath.com under several trade names including inter alia FREEZOR® MAX Cardiac CryoAblation Catheter, and ARCTIC FRONT® Cardiac CryoAblation Catheter. The cryocatheters employ nitrous oxide or argon refrigerant and are capable of heat transfer of several dozens of watts of thermal energy from human tissue over a period of 4 to 5 minutes for freezing a catheter tip to as low as −150° C. to create a so-called ice ball of up to a size of 20 mm diameter for high cryoenergy purposes, for example, cryoablation, and the like. The cryocatheters are also operated at partial cryocapacities for low and mid cryoenergy purposes, for example, ice mapping procedures at a typically narrow temperature range of −10° C. to −20° C., and the like. The cryocatheters are considered to be less steerable than their non-cryo counterparts because of their construction to withstand high pressure which can lead to greater difficulty to steer them to a desired therapy site. Moreover, the cryocatheters have a relatively large cryotemperature stability range of about +/−10° C. and are highly expensive.

Stroke hemorrhages are an acute neurologic injury occurring as a result of bleeding into the brain. There are two distinct mechanisms: bleeding directly into the brain parenchyma known as IntraCerebral Hemorrhage hereinafter referred to as ICH, or bleeding into the CerebroSpinal Fluid (CSF) between the brain and the skull known as SubArachnoid Hemorrhage hereinafter referred to as SAH. In most of cases, it results from a weakened vessel that ruptures and bleeds into the surrounding brain such as the Middle Cerebral Artery (MCA) area. Blood accumulates and compresses the surrounding brain tissue which may lead to severe damage of the tissue, permanent brain injury or even a death. According to the World Health Organization, approximately 30 million people had a stroke in the year 2000. 15% of patients were diagnosed with stroke hemorrhages (4.5 million people).

Treatment depends substantially on the type of a stroke and includes both medication and surgery. Main medications include antihypertensive drugs such as beta blockers and blood coagulators. Surgery procedures include, for example, craniotomy, namely, cutting a hole in the skull, and aneurysm clipping. This is suitable only for SAH in the areas proximal to the skull. As of today, there isn't an effective minimal invasive procedure to close off a ruptured blood vessel in ICH cases.

SUMMARY OF THE INVENTION

The present invention is directed towards cryocatheter systems and cerebral medical procedures employing local ice balls. The cryocatheter systems include cryocatheters having an elongated flexible catheter member and a short rigid catheter tip for cryotherapy at a therapy site. The catheter tips are typically introduced into a human lumen via an externally accessible access port to be pushed therealong to a therapy site for cryotherapy thereat before being pulled back along the human lumen to leave therefrom at the access port in a single clinical procedure. The cryocatheters of the present invention include at least one thermoelectric module for directly freezing an external surface of a catheter tip to a cryo-temperature of from −10° C. to −30° C. in the immediate vicinity of a 37° C. human body temperature therapy site to temporarily freeze human tissue for a cryogenic procedure before defrosting same to permit removal of the cryocatheter from the human lumen. The cyrocatheters of the present invention additionally include a heat exchange arrangement in flow communication with an external coolant fluid source for providing a downstream coolant fluid flow for passing a coolant fluid flow therethrough for cooling a thermoelectric module hot side of the at least one thermoelectric module for freezing the catheter tip's exterior surface. The cryocatheter systems of the present invention can be implemented as either open irrigation cryocatheter systems or closed circuit cryocatheter systems. In both implementations of cryocatheter systems of the present invention, the coolant fluid remains in the same phase during the heat transfer process in contradistinction to the Joules Thomson effect.

Non-cryocatheters have long employed thermoelectric modules for cooling and/or heating a catheter tip for therapy at a therapy site. Exemplary prior art patent publications include inter alia U.S. Pat. No. 7,238,184, WO 94/19833 entitled Thermoelectric Devices with Recuperative Heat Exchangers, WO 02/080766 entitled Treatment of Lipid Pool, and the like. Such non-cryocatheters have employed a range of heat sink techniques to cool a thermoelectric module hot side of a thermoelectric module opposite a thermoelectric module cold side of the thermoelectric module for cooling its catheter tip to below human body temperature but far above the cryo-temperatures achievable by the cryocatheters of the present invention. Heat sink techniques include inter alia a conductive solid core heat sink, the use of a blood pool in the immediate vicinity of a therapy site, and the like.

WO 02/080766 page 6 line 11 discloses a catheter assembly 70 having a "cold" bottom side 200 having a "cold" bottom side 200 for solidifying or "freezing" inflamed and unstable lipid pools 110 located within artery 100. WO 02/080766 catheter assembly 70 could employ thermoelectric modules, for example, commercially available from TEC Microsystems GmbH, Berlin-Adlershof, Germany, www.tecmicrosystems.com. Suitable thermoelectric modules include inter alia 1MD03-008-4, 1MD03-036-4 and the like, which have a 25% to 30% thermal efficiency at a 30° C. to 40° C. temperature difference across their thermoelectric module hot and cold sides. Larger temperature differences across a thermoelectric module considerably deteriorate its thermal efficiency and are considered unpractical. The WO 02/080766 catheter assembly 70 is cooled by blood flow and accordingly it can be shown that the aforesaid thermoelectric modules operating at, say, 15% to 20% thermal efficiency are capable of cooling the bottom side 200 to, say, about 10° C. sufficient to solidify inflamed or unstable lipid pools but incapable of cooling the bottom side 200 to sub-zero temperatures.

The present invention is based on the realization that it is possible to design heat exchange arrangements for sufficient heat transfer from a thermoelectric module hot side over a 3 to 4 minute duration to freeze an exterior surface of a catheter tip to a cryo-temperature in the region of from $-10°$ C. to $-30°$ C. in the immediate vicinity of a 37° C. human body temperature therapy site for producing different shapes and different dimensions of frozen human tissue at a therapy site. Such cryocapability is capable of freezing human tissue to form ice balls of 6.0 mm to 8.0 mm diameter suitable for low and mid cryoenergy cryotherapy procedures, for example, blocking biological activity in the human tissue, providing a 50 gram anchoring force, and the like. Cryocatheters of the present invention are incapable of supplying the same high cryogenic energy as aforesaid described Joule-Thomson cryocatheters but it is envisaged they will be considerably less expensive than the Joule-Thomson cryocatheters and therefore the preferred option for low and mid cryoenergy cryotherapy procedures. Moreover, the thermoelectric module based cryocatheters of the present invention are more readily controllable than Joule-Thomson effect cryocatheters.

It can be shown that it requires heat transfer from about 1.5 Watt to about 2.0 Watt thermal energy over a duration of 3 to 4 minutes to freeze local human tissue to from about $-10°$ C. to about $-25°$ C. at a 37° C. human body temperature therapy site. Accordingly, based on an aforesaid practical 30% thermal efficiency, a heat exchange arrangement of the present invention is required to heat transfer from about 6.5 Watt to 7.5 Watt thermal energy from a thermoelectric module hot side of an at least one thermoelectric module. This thermal energy takes into account the thermal energy needed to be absorbed from the human tissue to be frozen and the electrical energy applied to operate the at least one thermoelectric module. In order for a thermoelectric module cold side of a thermoelectric module to have a cryo-temperature of between from about $-10°$ C. to $-30°$ C., its thermoelectric module hot side has to have a temperature of about 10° C. as dictated by aforesaid 30° C. to 40° C. temperature difference across a thermoelectric module hot side and a thermoelectric module cold side. The downstream coolant fluid flow can be cooled to no less than near freezing temperature of, say, about 3° C. to prevent its possible freezing before delivery to a catheter tip. Accordingly, the downstream coolant fluid flow has a downstream temperature, of say, about 5° C. on average after its delivery to a catheter tip to leave an about 5° C. temperature difference between the downstream coolant fluid flow and a thermoelectric module hot side. Depending on lengthwise or widthwise deployment of a thermoelectric module in a catheter tip, its thermoelectric module hot side has a hot side footprint area of $20\pm10$ mm$^2$ Lengthwise and widthwise deployments of a thermoelectric module are correspondingly co-directional with or transverse to a longitudinal axis of a catheter member. Typically lengthwise thermoelectric modules have greater hot side footprint areas than widthwise thermoelectric modules. Accordingly, the heat exchange arrangement of the present invention is necessarily designed to be able to absorb 7.5 W thermal energy from a $20\pm10$ mm$^2$ thermoelectric module hot side which represents a considerable heat density dissipation of from about 250 Kw/m$^2$ to 750 Kw/m$^2$.

The present invention includes two types of heat exchange arrangements to achieve this high degree of heat transfer as follows: First, a so-called heat sink module. And second, a so-called jet impingement module.

The former includes a heat sink in thermal energy connection with a thermoelectric module hot side of an at least one thermoelectric module. The heat sink is made from highly heat conductive materials typically having a heat conduction coefficient of at least 170 w/m° C. Suitable materials include inter alia metal, carbon based thermal conductive materials, and the like. The heat sink is designed with a total heat exchange area of at least four times greater than the hot side footprint area in order to absorb the about 7.5 Watt thermal energy. The present invention envisages several different implementations of heat sinks as follows: A finned heat sink. A coil heat sink. A heat sink stack of wire mesh discs. A porous heat sink.

The latter employs a coolant fluid supply line providing one or more coolant fluid jets preferably directly against a thermoelectric module hot side in order to heat transfer the 7.5 Watt thermal energy from the thermoelectric module hot side. Reference is made to two jet impingement papers regarding the principles of the use of jets for thermal energy dissipation which are incorporated herein by reference. The jet impingement papers are as follows: Local Heat Transfer to Impinging Liquid Jet in the Initially Laminar, Transitional and Turbulent Regimes" by B. Elison and B. W. Webb, Journal of Heat and Mass Transfer Vol. 37 No. 8, 1994. Convective Heat Transfer by Impingement of Circular Liquid Jets" by X. Liu and J. H. Lienhard and J. S. Lombara, Journal of Heat Transfer, August 1991, Vol. 113/571. Alternatively, a thermoelectric module hot side may be covered by an impingement plate in direct thermal contact with its underlying thermoelectric module hot side.

In the case of open irrigation cryocatheter systems, coolant fluid is open irrigated into an internal human surrounding at a therapy site and therefore the coolant fluid is necessarily a bio-compatible liquid, for example, 0.9% NaCl saline, and the like. In the case of closed circuit cryocatheter systems, a cryocatheter includes a coolant fluid return line co-extensive with a coolant fluid supply line for transporting coolant fluid from a catheter tip to an external coolant fluid destination. The coolant fluid destination is preferably connected to the coolant fluid source for recirculation. The coolant fluid is not necessarily a bio-compatible liquid and it can alternatively be a gas, for example, nitrous oxide, argon, and the like.

The cyrocatheters of the present invention can deploy one or more thermoelectric modules either lengthwise and/or widthwise in a catheter tip. The thermoelectric modules of a cryocatheter in accordance with the present invention can include a single Peltier device or a stack of two or more Peltier devices with a thermoelectric module hot side of one Peltier device facing the thermoelectric module cold side of another Peltier device.

The cryocatheters of the present invention are particularly suitable for cerebral medical procedures by virtue of their high flexibility enabling their navigation along small size lumens typical to brain arteries and veins and also their precise temperature control better than +/−1° C. compared with the Joule-Thompson cryogenic catheter stability of typically +/−10° C. Because of the delicate nature of brain tissue, a cryocatheter system is required to be operated such that its catheter tip forms an ice ball of a specific size and is maintained within a narrow temperature range such that brain tissue temperatures in a frozen zone stay above −15° C. such that after defrosting a therapy site, the previously frozen brain tissue will revert to its normal biological and electrical activity. Too low a temperature in a frozen zone may cause a cold lesion causing permanent brain damage. The cerebral medical procedures include inter alia employing a local ice ball for sealing a bleeding rupture in an arterial wall in the case of a stroke hemorrhage, employing a local ice ball for mapping electrical disorder foci in a brain, for example, epileptic foci, and the like.

BRIEF DESCRIPTION OF DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE INVENTION

Figures 1, 2:
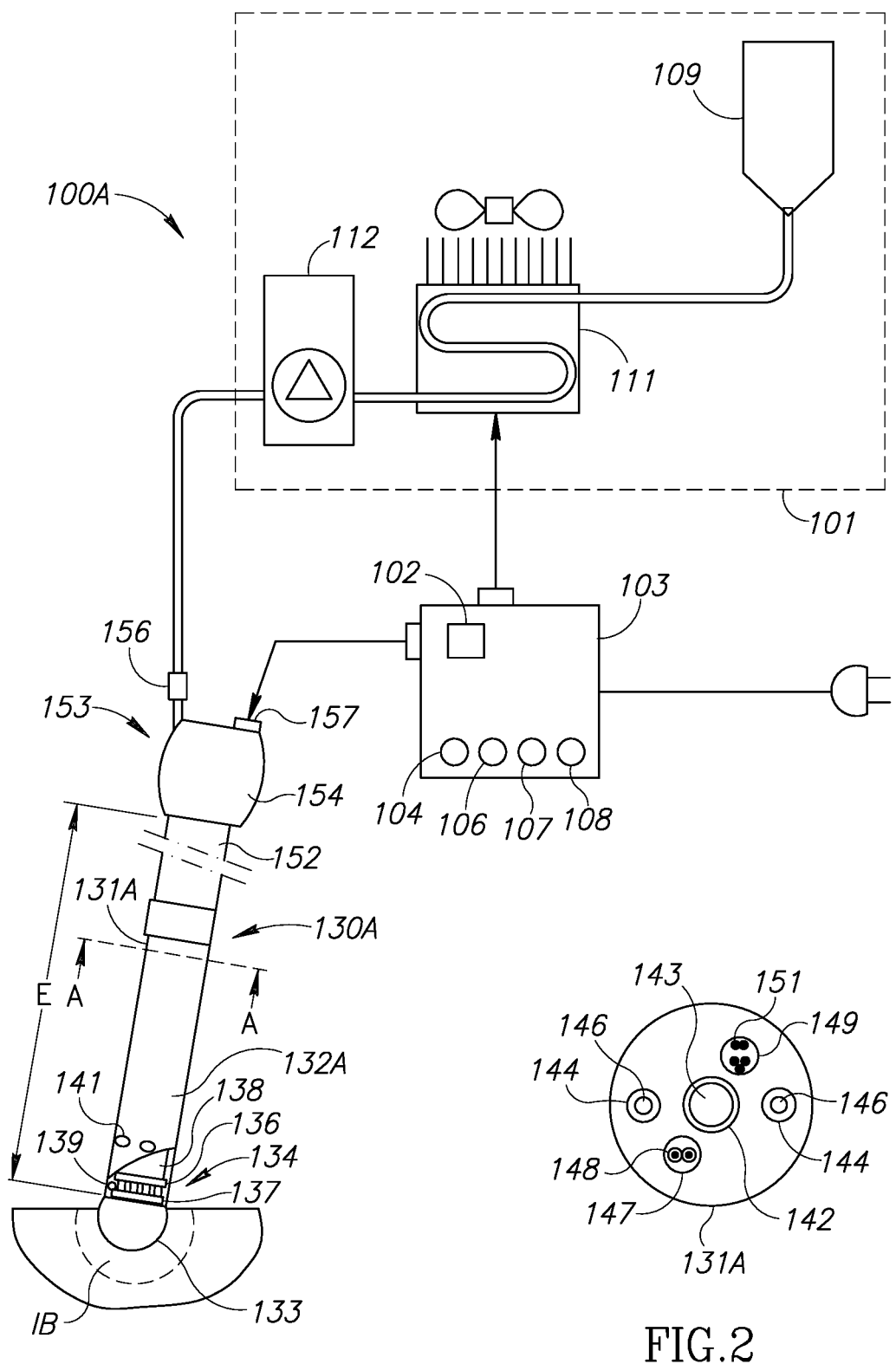
FIG. 1 is a block diagram of an open irrigation cryocatheter system including an open irrigation cryocatheter including a widthwise thermoelectric module and a heat exchange arrangement for forming an ice ball at a therapy site in accordance with a first aspect of the present invention.
FIG. 2 is a transverse cross section of FIG. 1's open irrigation cryocatheter along line A-A in FIG. 1.

FIG. 1 shows an open irrigation cryocatheter system 100A for use with an open irrigation cryocatheter 130A including an open irrigation elongated flexible catheter member 131A and an open irrigation short rigid catheter tip 132A for forming an ice ball IB at a therapy site. The cryocatheter system 100A necessarily employs a bio-compatible liquid for cooling purposes in view of open irrigation into internal human tissue at a therapy site. The bio-compatible liquid is preferably 0.9% NaCl saline, and the like.

The catheter member 131A has an about 0.5 m to 1.5 m length denoted E depending on its intended cryotherapy application. The catheter tip 132A has an about 0.4 cm to 1.5 cm length. The catheter member 131A and the catheter tip 132A have an about 1.65 mm to 3.3 mm outside diameter. The catheter tip 132A terminates at a leading catheter dome 133. The catheter dome 133 can have a smooth spherical shape. Alternatively, the catheter dome 133 can be formed with different finishes and shapes similar to commercially available RF ablation catheters and diagnostic catheters. For example, Medtronic FREEZOR® cryoablation catheter and St. Jude Medical's INQUIRE® diagnostic catheter have different shaped catheter domes 133.

The catheter tip 132A includes a widthwise thermoelectric module 134 transverse to a longitudinal axis of the catheter member 131A. Suitable thermoelectric modules 134 include, for example, TEC Microsystems GmbH part number 1MD03-008-4 commercially available from TEC Microsystems GmbH, Berlin-Adlershof, Germany, www.tecmicrosystems.com. The thermoelectric module 134 has a thermoelectric module hot side 136 and a thermoelectric module cold side 137 during its operation for freezing the catheter tip 132A. The catheter tip 132A includes a heat exchange arrangement 138 for heat transfer from the thermoelectric module hot side 136. The catheter tip 132A includes a thermistor 139 for monitoring the temperature of the thermoelectric module hot side 136 or the thermoelectric module cold side 137. The catheter tip 132A includes one or more irrigation holes 141 for enabling flow of coolant fluid from the catheter tip 132A to an internal human surrounding at the therapy site. The catheter tip's 132A heat exchange arrangement 138 can be implemented as either a heat sink module or a jet impingement module as described hereinbelow.

The catheter dome 133 is in highly thermal conductive contact with the thermoelectric module cold side 137 for freezing human tissue to form the ice ball IB. The catheter dome 133 is formed from bio-compatible highly thermal conductive materials with a thermal conductivity coefficient k of at least >50 w/m° C. and preferably higher. Suitable catheter dome materials include metals, for example, platinum, iridium, gold, etc and highly conductive plastics. Gold is particularly suitable for some applications since it has an extremely high thermal conductivity coefficient k>250 w/m° C. The catheter dome 133 is preferably glued onto the thermoelectric module cold side 137 using a highly thermal conductive filling material to reduce a temperature drop from the thermoelectric module cold side 137 to the catheter dome 133. Suitable commercially available high grade gap filling materials have a high thermal conductivity coefficient k in the range of about 10 w/m° C.

FIG. 2 shows the catheter member 131A has an extruded construction including the following longitudinal lumens: First, a central lumen 142 for housing a coolant fluid supply line 143 for delivering a downstream coolant fluid flow to the catheter tip 132A. Second, a pair of opposite lumens 144 for housing steering wires 146 for assisting the navigation of the catheter tip 132A to a therapy site. Third, a lumen 147 for housing an electrical power lead pair 148 connected to the thermoelectric module 134. And fourth, a lumen 149 for housing a thermistor lead pair 151 connected to the thermistor 139. The lumen 149 can also be employed for housing additional control wires.

The cryocatheter system 100A includes an external coolant fluid source 101 for delivering bio-compatible coolant fluid to the cryocatheter 130A for freezing the catheter tip 132A, a thermoelectric module power source 102 connected to the electrical power lead pair 148 and a controller 103 for controlling the operation of the external coolant fluid source 101 and the thermoelectric module power source 102. The controller 103 includes an ON/OFF switch 104, an ICING control 106 for freezing the catheter tip 132A and a DEFROST control 107 for defrosting the catheter tip 132A and a TEMPERATURE level control 108. The controller 103 is connected to the thermistor lead pair 151. The DEFROST control 107 reverses the polarity of the electrical power lead pair 148 for cooling the thermoelectric module hot side 136 and the heating the thermoelectric module cold side 137.

The external coolant fluid source 101 includes a coolant fluid reservoir 109, for example, a 0.9% NaCl saline infusion bag at 17° C. to 24° C. ambient temperature. The external coolant fluid source 101 includes a cooling device 111 for cooling the saline to preferably near freezing temperature, say, 3° C. to 4° C. to ensure the saline does not freeze. The cryocatheter system 100A is operable at higher coolant fluid temperatures, say, 10° C. but this linearly reduces its cryo-capability. The external coolant fluid source 101 also includes a peristaltic pump 112 for delivering the downstream coolant fluid flow to the cryocatheter 130A at an acceptable maximal flow rate of about 35 cc/min in view of open irrigation to an internal human surrounding.

The coolant fluid supply line 143 has a typical internal diameter in the range of 0.4 mm to 0.7 mm. The fluid velocity of the downstream coolant fluid flow in the coolant fluid supply tube 143 is about 1.5-4.5 m/s such that it has a Reynolds number of about 700-1200 in the laminar range. This flow rate typically causes a pressure drop as high as 40-70 psi which is near the maximum allowable for standard medical grade tubing set.

The catheter member 131A has a proximal end 152 opposite its leading catheter tip 132A including a termination arrangement 153. The termination arrangement 153 can include a handle 154 connected to the steering wires 146, a Luer connection 156 for connection to the external coolant fluid source 101 and an electrical connector 157 for connection to the controller 103.

Figures 3, 4:
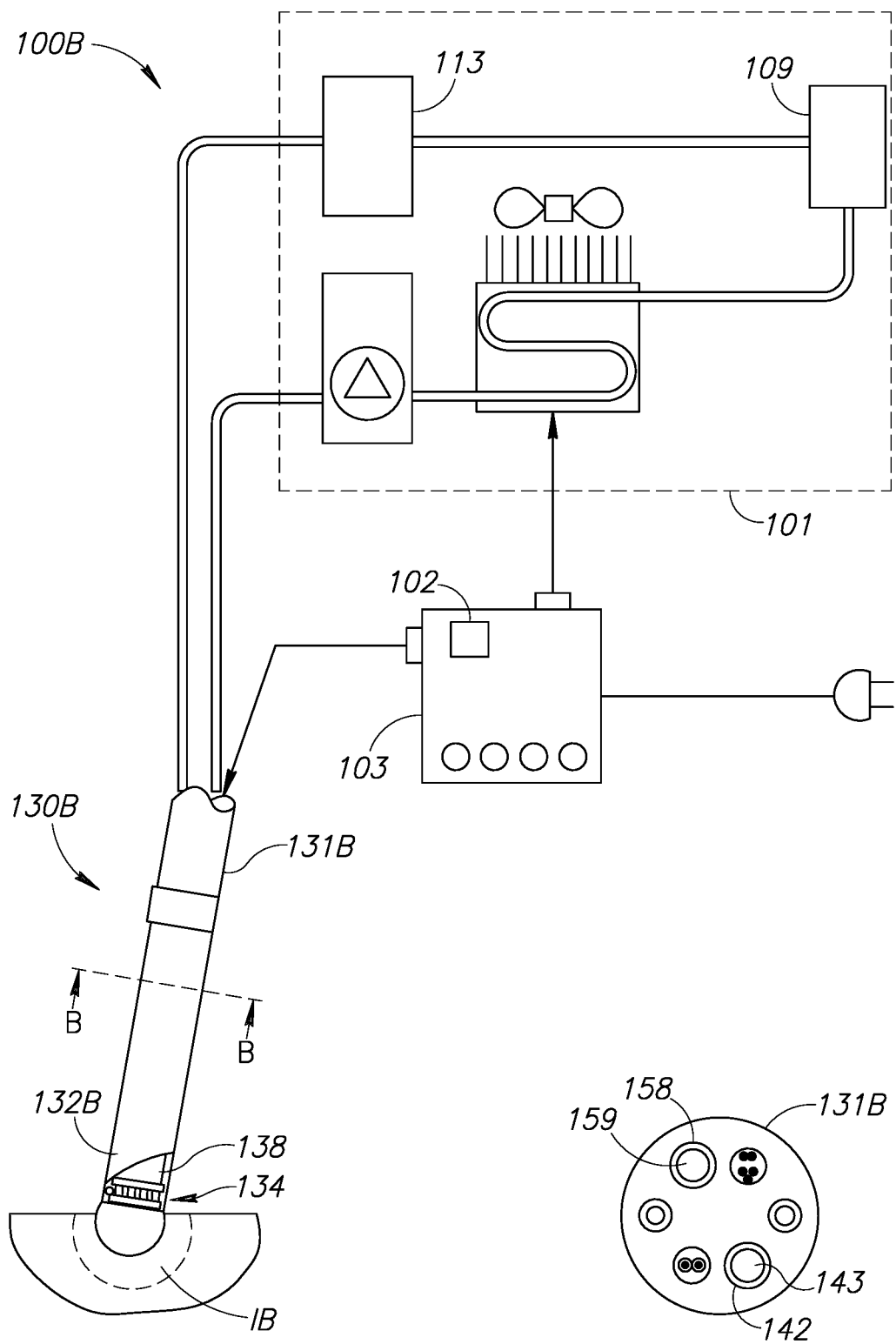
FIG. 3 is a block diagram of a closed circuit cryocatheter system including a closed circuit cryocatheter for forming an ice ball at a therapy site.
FIG. 4 is a transverse cross section of FIG. 3's closed circuit cryocatheter along line B-B in FIG. 3.

FIG. 3 show a closed circuit cryocatheter system 100B including a closed circuit cryocatheter 130B having a closed circuit catheter member 131B and a closed circuit catheter tip 132B for forming an ice ball IB at a therapy site. The closed circuit cryocatheter system 100B is similar in construction and operation to the cryocatheter system 100A and therefore similar parts are likewise numbered. The closed circuit cryocatheter system 100B can employ a coolant fluid in the form of gas, vapor or liquid as opposed to the open irrigation cryocatheter system 100A. The present cryocatheter system 100B is described with reference to a liquid coolant. A cryocatheter system 100B employing a gas coolant can be readily modified from the present system. A gas based cryocatheter system 100B includes a gas pump instead of the peristaltic pump. A gas based cryocatheter system 100B operates at high pressure but not as high as Joule-Thomson effect cryocatheter systems.

The closed circuit cryocatheter system 100B differs from the open irrigation cryocatheter system 100A insofar as the former 100B includes a coolant fluid destination 113. The cryocatheter 130B differs from the cryocatheter 130A insofar as the former's catheter member 131B includes another lumen 158 for housing a coolant fluid return line 159 (see FIG. 4) and its catheter tip 132B does not have irrigation holes. The coolant fluid return line 159 is connected to the coolant fluid destination 113 which is in turn preferably connected to the coolant fluid reservoir 109. The coolant fluid supply line 143 and the coolant fluid return line 159 typically have a smaller cross section area in the cryocatheter 130B in comparison to the cryocatheter 130A's coolant fluid supply line 143 due to external cryocatheter diameter constraints. The catheter tip 132B's heat exchange arrangement 138 can be implemented as either a heat sink module or a jet impingement module to cool the thermoelectric module hot side 136 as described hereinbelow.

The use of the cryocatheter system 100A is as follows:

A surgeon introduces the catheter tip via an externally accessible access port into a human lumen. The surgeon navigates the catheter tip to a therapy site. The surgeon switches the controller to ICING mode for about 3 to 5 minutes to freeze the catheter tip at the therapy site. The catheter tip freezes human tissue at the catheter tip to form an ice ball which binds the human tissue to the catheter tip. The freezing process itself may be the desired cryotherapy or alternatively a surgeon may perform an additional medical procedure. At the end of the medical procedure, the surgeon switches the controller to DEFROST mode for about 30-60 second to defrost the human tissue at the catheter tip to prevent tissue laceration particularly in a vascular procedure if a catheter tip is pulled from human tissue while still iced thereto.

Thermodynamic Analysis of the Heat Exchange Arrangement

The heat exchange arrangement 138 has an incoming downstream coolant fluid flow and an outgoing coolant fluid flow to either internal human surroundings in an open irrigation cryocatheter system 100A or a coolant fluid destination 113 in a closed circuit cryocatheter system 100B.

The heat exchange arrangement 138 has the following specification:

h: heat transfer coefficient

Ah: heat exchange area

The following symbols are used:

Q is the total thermal energy, namely, about 7.5 Watts, required to undergo heat transfer from a thermoelectric module hot side to a coolant fluid flow in a heat exchange arrangement. The total thermal energy Q=Q1+Q2 where Q1 is the human thermal energy required to be absorbed from the human tissue to be frozen and Q2 is the electrical energy required to operate the at least one thermoelectric module.

Tin is the temperature of an incoming downstream coolant fluid flow on arrival at the heat exchange arrangement 138. Tin is estimated at 4° C. to 5° C. based on its initial cooling to, say, 2° C. to 3° C. before introduction into a cryocatheter and its subsequent heating during its travel along a catheter member.

Tout is the temperature of an outgoing coolant fluid flow on leaving the heat exchange arrangement 138. Tout is estimated at 6° C. to 9° C. after being heated directly or indirectly by the thermoelectric module hot side 136.

Thot is the temperature of the thermoelectric module hot side 136 of the at least one thermoelectric module of a cryocatheter tip where $$T\text{hot} = T\text{in} + \Delta t1 + \Delta t2 + \ldots + \Delta tn \tag{1}$$

where $\Delta t1, \Delta t2 \ldots \Delta tn$ are temperature differences depending on a construction of a catheter tip and its heat exchange arrangement Tcold is the temperature of the thermoelectric module cold side 137 where for practical considerations $$T\text{cold} = T\text{hot} - 35° \text{ C.} \tag{2}$$

$\Delta t1$ is the convection temperature difference between a coolant fluid flow passing through the heat exchange arrangement 138 and a heat exchange area Ah calculated as follows:

$$\Delta t1 = \frac{Q}{h \times Ah} \tag{3}$$

The heat exchange arrangement 138 is required to be capable of developing a convection temperature difference $\Delta t1$ in the range of from about 4° C. to about 10° C. such that a heat exchange arrangement 138 is capable of heat transfer from a thermoelectric module hot side 136 for freezing an exterior surface of a catheter dome 133 to a cryo-temperature from between about −15° C. to about −30° C. for freezing human tissue at a therapy site.

The heat sink implementations of a heat exchange arrangement of the present invention have a relatively low heat transfer coefficient h and therefore are designed to have a large heat exchange area Ah compared to a thermoelectric module hot side footprint area Af. The jet impingement implementations of a heat exchange arrangement of the present invention have a relatively high heat transfer coefficient h and therefore can be designed to employ the available hot side footprint area Af of a thermoelectric module as the heat exchange area Ah without the need for additional heat exchange area as per heat sink implementations.

Heat Sink Implementations of Heat Exchange Arrangement

Figure 5:
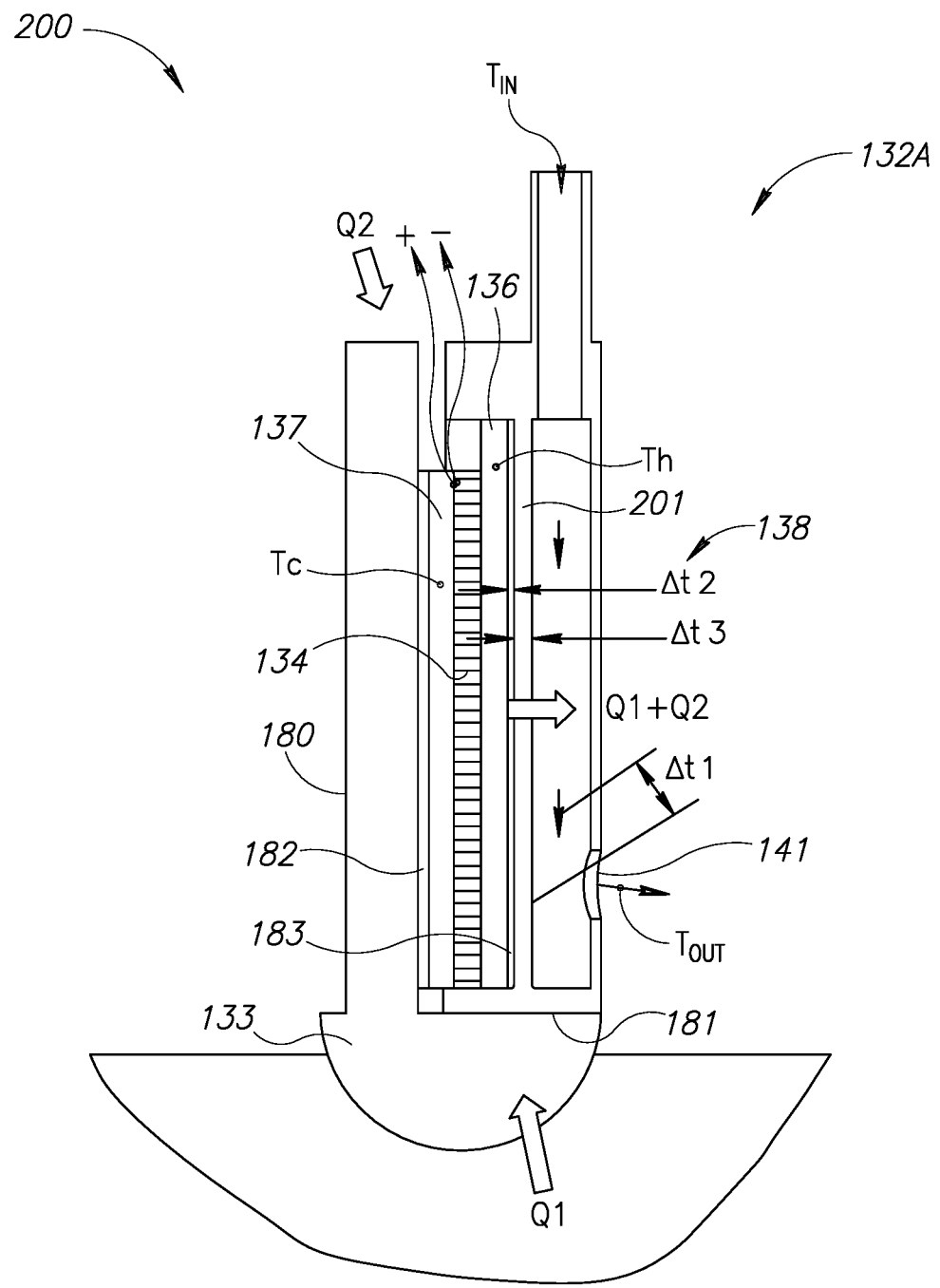
FIG. 5 is a longitudinal cross section of FIG. 1's catheter tip including a lengthwise thermoelectric module and a heat sink module.

FIG. 5 shows an open irrigation catheter tip 132A including a lengthwise thermoelectric module 134 co-directional with a longitudinal axis of the catheter member 131A and a heat sink module 200 constituting the heat exchange arrangement 138. An exemplary thermoelectric module 134 is the TEC Microsystems GmbH part number 1MD03-036-4 with a thermoelectric module hot side footprint area of a near 20 mm$^2$.

The catheter tip 132A is designed for ensuring minimal temperature differences across adjacent components to facilitate freezing of human tissue. Accordingly, the catheter tips 132A employs high grade gap filling material having a thermal conductivity coefficient k in the range of about 10 w/m° C. Suitable gap filling material includes inter alia AI technology, Inc.'s Ultra high thermally conductive epoxy paste adhesive ME7159 www.aithecnology.com.

The catheter tip 132A includes a catheter side wall 180 with a lengthwise cutout 181 extensive with the catheter side wall 180 for receiving the lengthwise thermoelectric module 134 and the heat sink module 200. The thermoelectric module 134 has a thermoelectric module hot side 136 opposite a thermoelectric module cold side 137 facing the catheter side wall 180 to freeze the catheter side wall 180 to freeze the catheter dome 133. The catheter tip 132A includes a first gap filling material layer 182 for mounting the thermoelectric module cold side 137 on the catheter side wall 180 and a second gap filling material layer 183 for mounting the heat sink module 200 on the thermoelectric module hot side 136. The gap filling material layers 182 and 183 have a thickness L typically in the range of from 50 µm to 100 µm. The heat sink module 200 has a lowermost wall 201 facing the thermoelectric module hot side 136.

This catheter tip construction introduces two additional temperature differences Δt2 and Δt3 such that the hot side temperature Thot is calculated as follows:

$$T\text{hot}=T\text{in}+\Delta t1+\Delta t2+\Delta t3 \quad (1)$$

where Δt2 is the temperature difference across the second gap filling layer 183 and is calculated as follows:

$$\Delta t2 = \frac{Q1 \times L}{K \times Af}$$

and where Δt3 which is the temperature difference across the lowermost surface 201 of the heat sink module 200 and is estimated to be 3° C. due to the very high heat flux density of about 400 Kw/m$^2$ from the thermoelectric module hot side 136 to the lowermost wall 201.

Assuming the heat sink module 200 has a heat transfer coefficient h=10000 w/m$^2$° C. and a heat exchange area Ah equal to the thermoelectric module's hot side footprint area of 20 mm$^2$=20×10$^{-6}$ m$^2$, then according to equation (3).

$$\Delta t1 = \frac{Q}{h \times Ah} = \frac{7.5}{10000 \times 20 \times 10^{-6}} \cong 37°$$

Based on the above technical details, Δt2 is calculated as follows:

$$\Delta t2 = \frac{7.5 \times 50 \times 10^{-6}}{10 \times 20 \times 10^{-6}} = 2° \text{ C.}$$

On substitution of the values of Tin, Δt1, Δt2 and Δt3 into equation (1), the thermoelectric module hot side 136 has a hot side temperature Thot as follows:

$$T\text{hot}=T\text{in}+\Delta t1+\Delta t2+\Delta t3=5° \text{ C.}+2° \text{ C.}+3° \text{ C.}+37° \text{ C.}=47° \text{ C.}$$

such that its thermoelectric module cold side 137 has an above freezing temperature according to equation (2):

$$T\text{cold}=T\text{hot}-35° \text{ C.}=47° \text{ C.}-35° \text{ C.}=+12° \text{ C.}$$

For illustrative purposes, to freeze the catheter tip 132A to −17° C., the hot side temperature Thot has to be capped at 18° C. This can be achieved by provision of a heat sink module 200 having a heat exchange area Ah of 94 mm$^2$ such that the convection temperature difference Δt1 is:

$$\Delta t1 = \frac{Q}{h \times Ah} = \frac{7.5}{10000 \times 94 \times 10^{-6}} \cong 8° \text{ C.}$$

and the hot side temperature Thot is therefor:

$$T\text{hot}=T\text{in}+\Delta t1+\Delta t2+\Delta t3=5° \text{ C.}+2° \text{ C.}+3° \text{ C.}+8° \text{ C.}=18° \text{ C.}$$

resulting in the desired thermoelectric module cold side cryo temperature:

$$T\text{cold}=T\text{hot}-35° \text{ C.}=18° \text{ C.}-35° \text{ C.}=-17° \text{ C.}$$

The first gap filling material layer 182 mounting the thermoelectric module cold side 137 on the catheter side wall 180 transfers the human thermal energy Q1 to be absorbed from the human tissue to be frozen to the heat exchange arrangement 138. As mentioned above, Q1 is between about 1.5 W and 2 W which is about a quarter of the thermal energy Q required to be dissipated from the thermoelectric module hot side 136 to the heat exchange arrangement 138. The first gap filling material layer 182 leads to a negligible about 0.5° C. temperature drop thereacross such that catheter side wall 180 and the catheter dome 133 are nearly the same temperature as the thermoelectric module cold side 137.

FIGS. 6 to 14 show five different heat sink modules 200 which can be readily designed to have a heat exchange area of at least four times greater than the hot side footprint area of a thermoelectric module.

Figure 6:
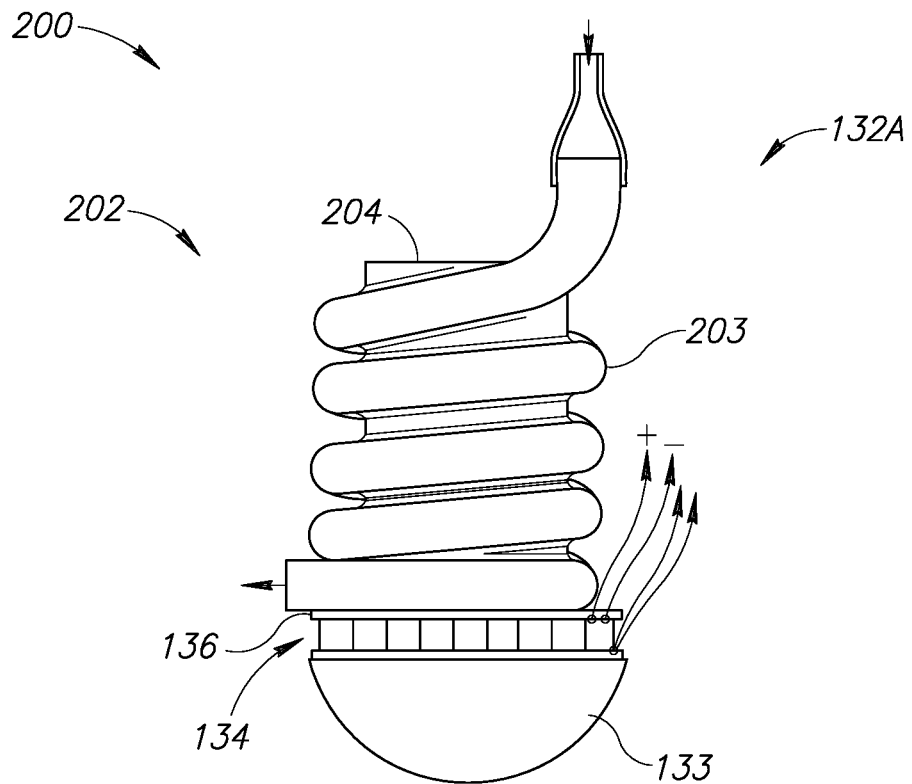
FIG. 6 is a longitudinal cross section of FIG. 1's catheter tip including a widthwise thermoelectric module and a coil heat sink.
Figure 7:
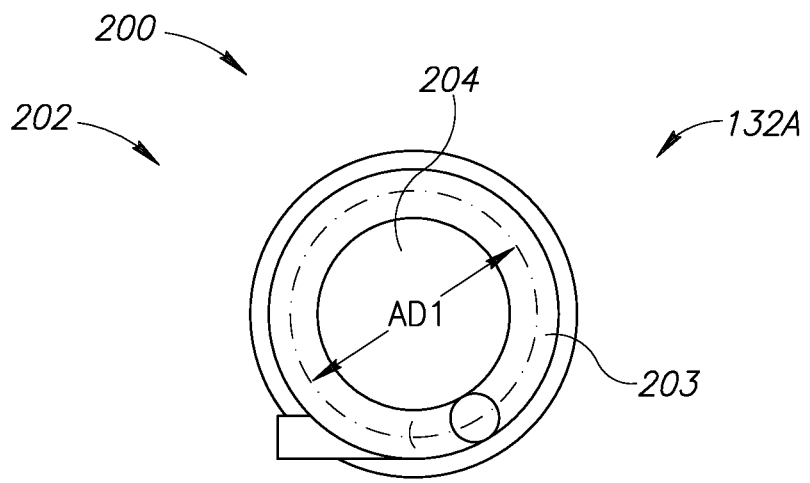
FIG. 7 is a top elevation view of a FIG. 6's coil heat sink.

FIGS. 6 and 7 show a catheter tip 132A with a widthwise thermoelectric module and a heat sink module 200 implemented as a coil heat sink 202. The coil heat sink 202 includes a coil 203 spiraled around a central cylindrical core 204 mounted on the thermoelectric module hot side 136. The coil 203 has an average diameter AD1 of about 2.5 mm and an overall tube length L1 where:

$$L1=\Pi \times AD1 \times N$$

where N is the number of turns around the core 204. A coil heat sink 202 with 8 turns has a heat exchange area Ah=Π× 0.5×63=99 mm².

Figure 8:
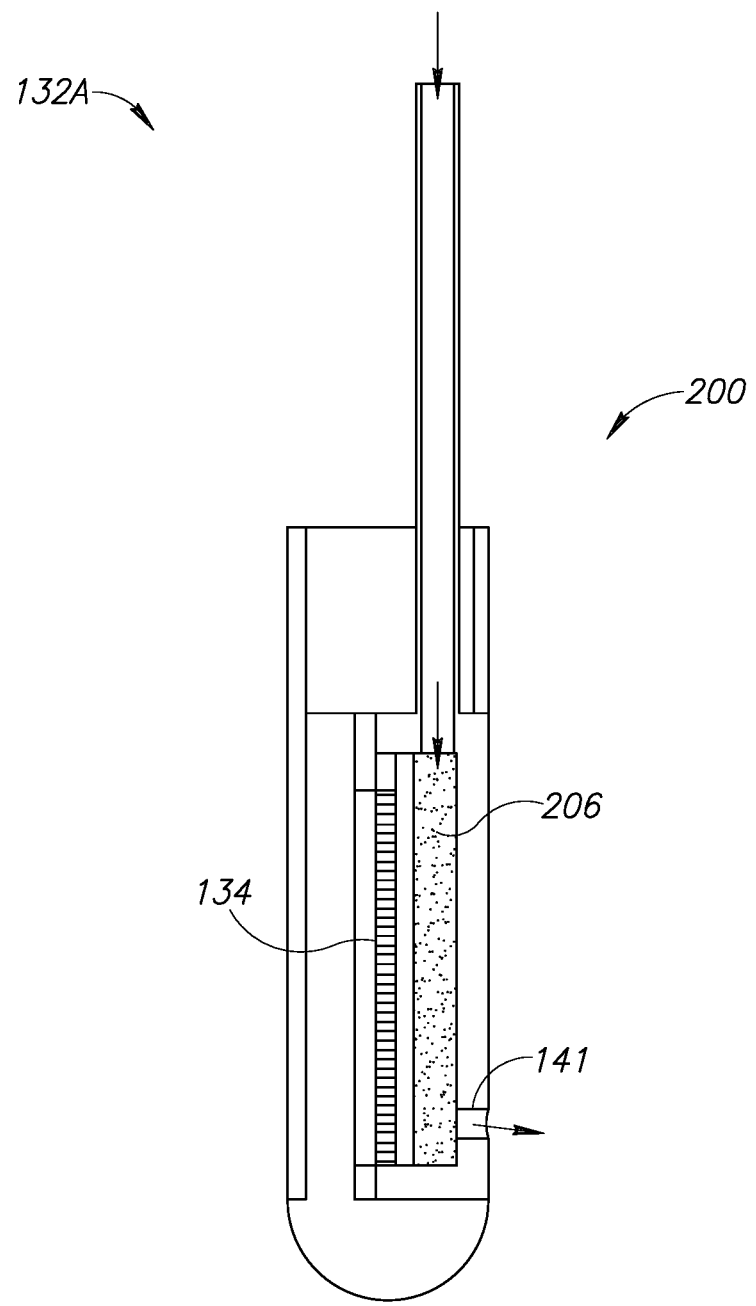
FIG. 8 is a longitudinal cross section of FIG. 1's catheter tip including a lengthwise thermoelectric module and a porous heat sink.

FIG. 8 shows a catheter tip 132A having a lengthwise thermoelectric module 134 and a heat sink module 200 implemented as a porous heat sink 206. The porous heat sink 206 can be formed from a range of thermal conductive materials such as metal, carbon based materials, and the like. The porous heat sink 206 has a heat exchange area determined by its material specific area (m²/gram).

Figure 9:
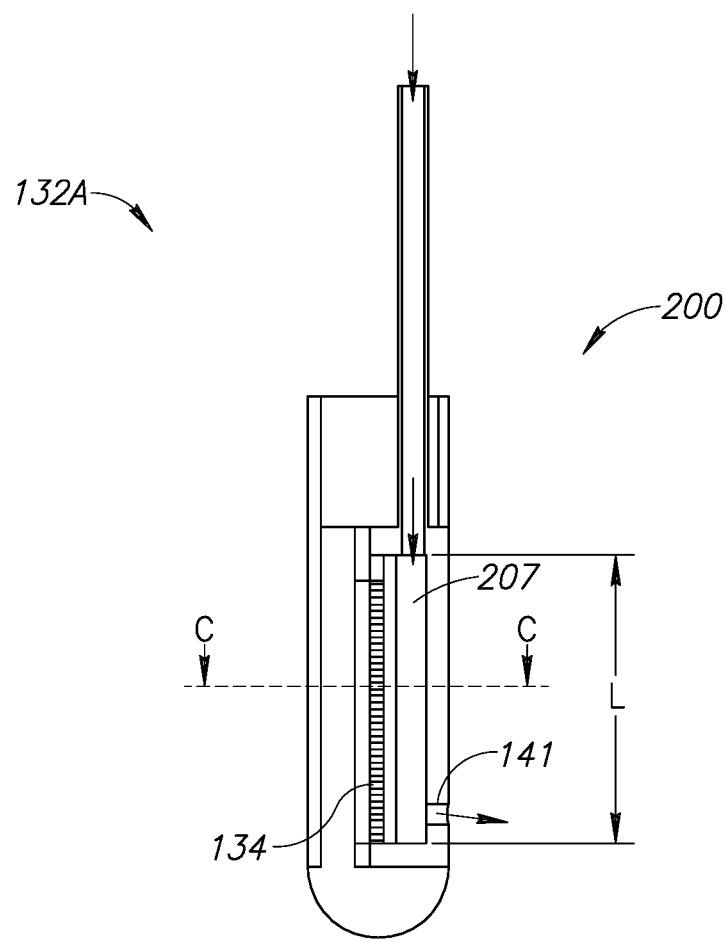
FIG. 9 is a longitudinal cross section of FIG. 1's catheter tip including a lengthwise thermoelectric module and a finned heat sink.
Figure 10:
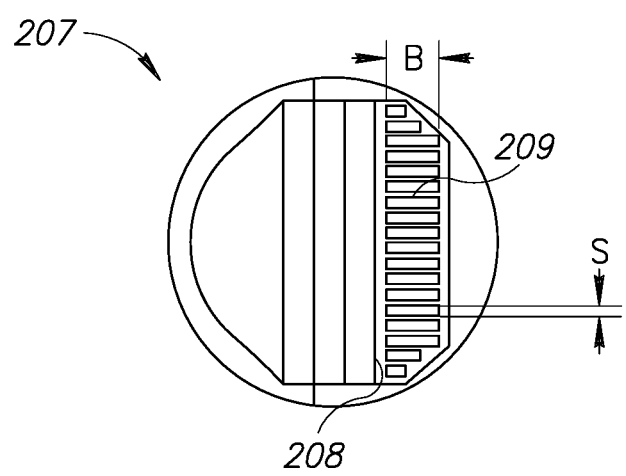
FIG. 10 is a transverse cross section of FIG. 9's finned heat sink along line C-C in FIG. 9.

FIGS. 9 and 10 show a catheter tip 132A having a lengthwise thermoelectric module 134 and a heat sink module 200 implemented as a finned heat sink 207. The finned heat sink 207 includes a base member 208 with a multitude of fins 209. The finned heat sink 207 has a heat exchange area Ah where Ah=2×[NF×B+(NF−1)×S]×L wherein NF is the number of fins, B is fin height, S is the spacing between fins and L is fin length.

Figure 11:
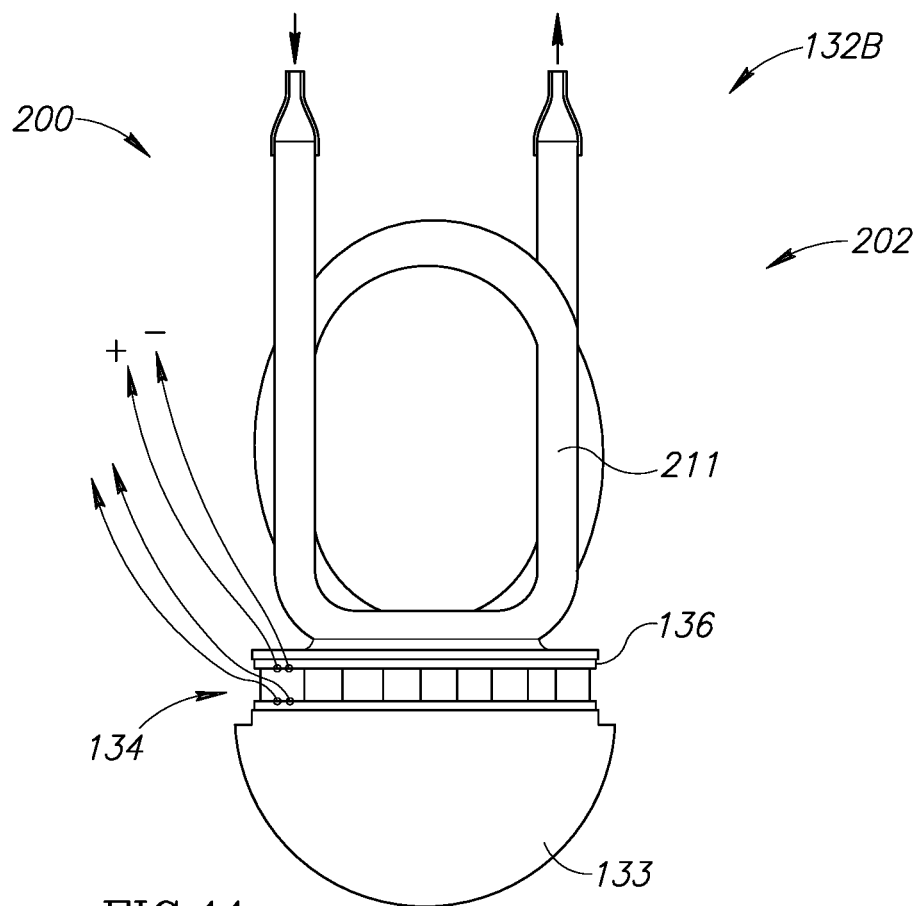
FIG. 11 is a longitudinal cross section of FIG. 3's catheter tip including a widthwise thermoelectric module and an alternative coil heat sink.
Figure 12:
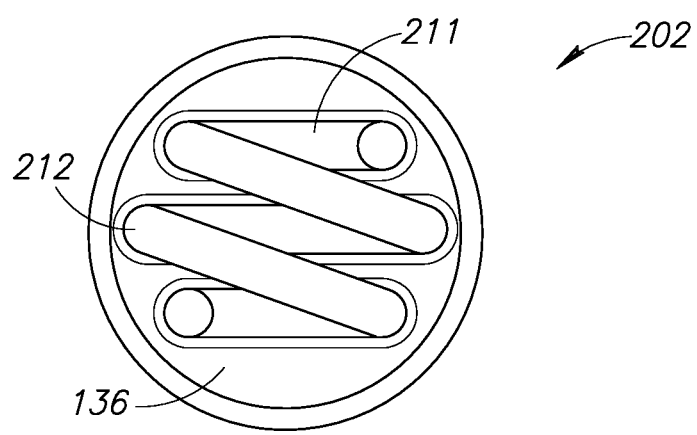
FIG. 12 is a top elevation view of FIG. 11's coil heat sink.

FIGS. 11 and 12 show a catheter tip 132B with a widthwise thermoelectric module 134 and a heat sink module 200 also implemented as a coil heat sink 202. The coil heat sink 202 includes a coil 211 with two or more windings 212 mounted on the thermoelectric module hot side 136 in a thermal conductive bonding process such as welding. The coil 211 has an internal tube diameter of about 0.5 mm and an overall tube length of between about 40 mm to −60 mm such that its heat exchange area equals is about 90 mm².

Figure 13:
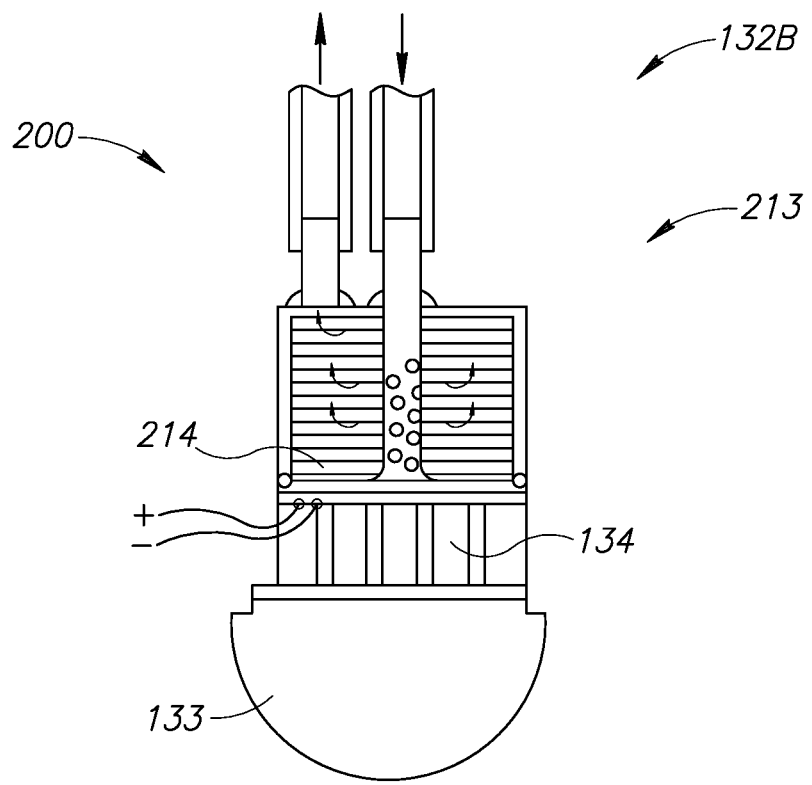
FIG. 13 is a longitudinal cross section of FIG. 3's catheter tip including a widthwise thermoelectric module and a heat sink stack of wire mesh discs.
Figure 14:
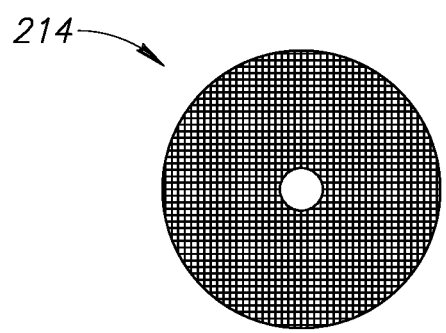
FIG. 14 is a top elevation view of a wire mesh disc of FIG. 13's heat sink stack.

FIGS. 13 and 14 show a catheter tip 132B with a widthwise thermoelectric module 134 and a heat sink module 200 implemented as a heat sink stack 213 of horizontal wire mesh members 214. FIGS. 13 and 14 show wire mesh members 214 in the form of wire mesh discs typically have an about 2 mm to 3 mm diameter and are formed from 0.11 mm thick metal. Heat sink stacks 213 can include equally upright wire mesh members. Wire mesh members can be formed in different shapes including inter alia rectangle, oval, and the like.

The wire mesh discs 214 typically have a mesh density of 100 wires per inch. For example, part number 100x100C0022W48T made from copper commercially available from TWP, Inc., Berkeley Calif. 94710, USA. The heat sink stack 213 includes about 30 discs with an overall height of 3 mm to 3.5 mm. The heat sink stack 213 has a heat exchange area determined by N×AS when N is the number of disks and AS is the overall surface area of each wire mesh disc.

Jet Impingement Implementations of Heat Exchange Arrangement

Jet impingement modules are based on impingement of one or more coolant fluid jets on an impingement surface for affording more efficient heat transfer than a heat sink module such that jet impingement modules are capable of freezing a catheter tip to colder cryo-temperatures than a heat sink module.

Figure 15:
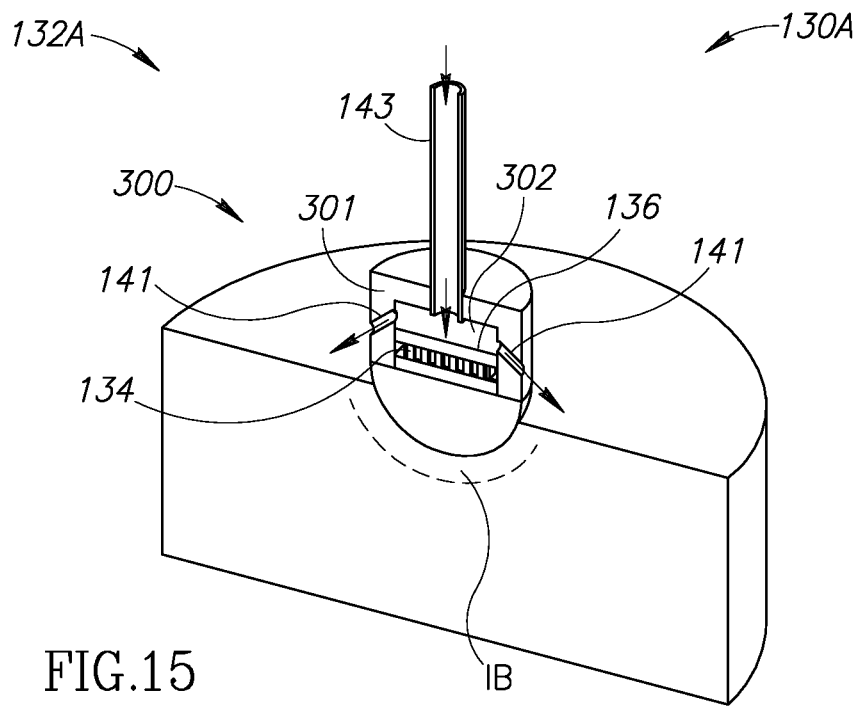
FIG. 15 is a perspective cross section of FIG. 1's catheter tip including a widthwise thermoelectric module and a jet impingement module with a single jet nozzle.
Figures 16A, 16B:
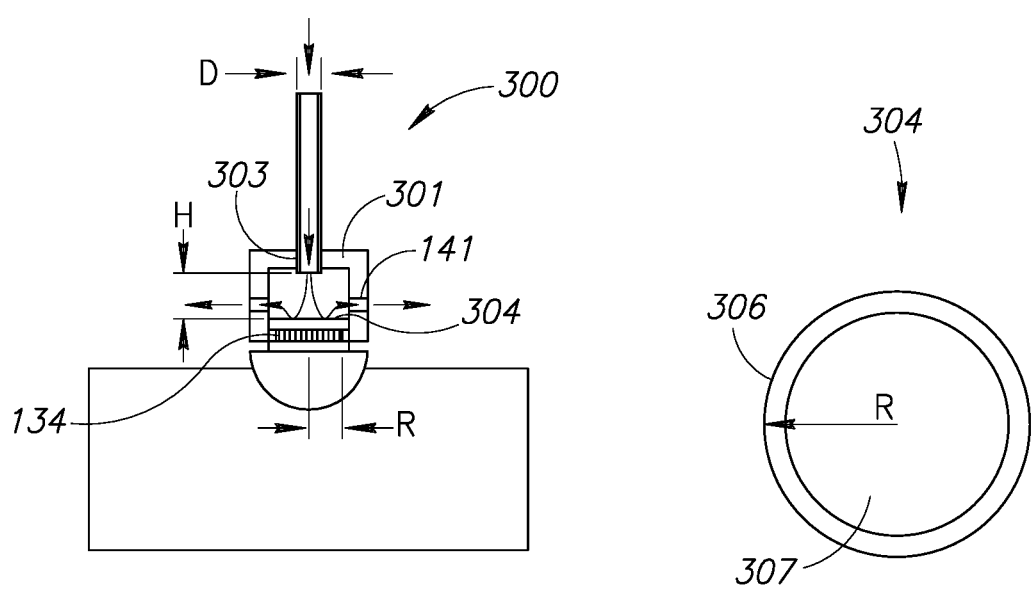
FIG. 16A is a front elevation view of FIG. 15's jet impingement module.
FIG. 16B is a top elevation view of an impingement zone of a jet nozzle of FIG. 15's jet impingement module on the thermoelectric module hot side.

FIGS. 15, 16A and 16B show an open irrigation cryo-catheter 130A having a catheter tip 132A with a widthwise thermoelectric module 134 and a jet impingement module 300 constituting the heat exchange arrangement 138 for forming an ice ball IB. The jet impingement module 300 includes a housing 301 sealed on the thermoelectric module 134 to form a heat exchange cavity 302. The housing 301 can be formed from non-thermally conductive material such as bio-plastics which is considerably less expensive than biocompatible materials such as platinum iridium, and the like. The housing 301 may be manufactured by suitable low cost processes for medical parts, for example, micro-injection molding. Moreover, because the housing 301 can be made from plastics with a low thermal expansion coefficient compatible with the ceramic plates of thermoelectric modules to reduce thermal stresses during operation.

The jet impingement module 300 includes a single jet nozzle 303 for impinging a coolant fluid jet preferably directly onto the thermoelectric module hot side 136 constituting the impingement surface at an impingement site 304. The jet nozzle 303 has an internal jet nozzle diameter D and an impingement height H from the thermoelectric module hot side 136. Jet nozzles typically have an internal jet nozzle diameter D in the range of 0.3 mm to about 0.7 mm and an impingement height H in the range of from about 0.3 mm to about 0.7 mm.

FIG. 16B shows each a coolant fluid jet causes heat transfer over an imaginary circular impingement zone 306 having an impingement zone radius R although the shape of an actual impingement zone 306 is bound by a housing 301. But each coolant fluid jet has an effective imaginary circular impingement zone 307 having a maximum impingement zone radius twice the size of an internal jet nozzle diameter D beyond which heat transfer is considerably reduced in the annular area between the impingement zones 306 and 307. Accordingly, it is thermodynamically worthwhile to add jet nozzles if R>3D to preferably eliminate any annular area beyond the impingement zone 307. Thus, jet impingement modules 300 can include a single jet nozzle 303 or an m×n array of jet nozzles 303 where at least one of m and n>1 depending on the size and dimensions of a thermoelectric module hot side 136.

The jet impingement module 300 has a heat transfer coefficient h which depends on two ratios as follows:

First, a ratio H/D which is preferably in the range of from about 0.5 to about 1.5 when the velocity of the coolant fluid jet exiting from the jet nozzle 303 is in the range of from about 1.5 msec to about 7.0 msec for maximal volumetric flow of 35 cc/min and a specific nozzle diameter.

And second, the ratio R/D preferably in the range of 2≤R/D≤4 because jet nozzles too close to each other complicate manufacturing and can cause their respective coolant fluid jets to interfere with one another.

The aforesaid jet impingement papers set out that a jet impingement module 300 has a heat transfer coefficient h according to equation:

$$h = \frac{Nu \times k}{D} \qquad (4)$$

where Nu is a so-called Nusselt number, k is the thermal conduction coefficient of jet impingement fluid and D is the internal jet nozzle diameter in meters. For example, 0.9% NaCl saline has a thermal conduction coefficient k≈0.58 w/m° C.

The aforesaid jet impingement papers also set out that a Nusselt number Nu is calculated according to equation (5):

$$Nu = 0.75 \times Re^{1/2} \times Pr^{1/3} \qquad (5)$$

where Re is a Reynold number and Pr is a Prantel number.

Jet impingement modules 300 in accordance with the present invention have a Reynold number in the range of from about 400 to about 1400, a Prantel number in the range of from about 9 to about 11 and a heat transfer coefficient h in the range of from about 35,000 w/m²° C. to about 55,000 w/m²° C. which is between three and six times larger than a heat sink module's heat transfer coefficient.

In contrast to the heat sink module 200, the jet impingement module 300 has a single temperature difference between the hot side temperature Thot and the coolant fluid, namely, the convection temperature difference Δt1 such that Thot=Tin+Δt1. The convection temperature drop Δt1 is calculated as per equation (3) where the heat exchange area A equals the hot side footprint area.

Figure 17:
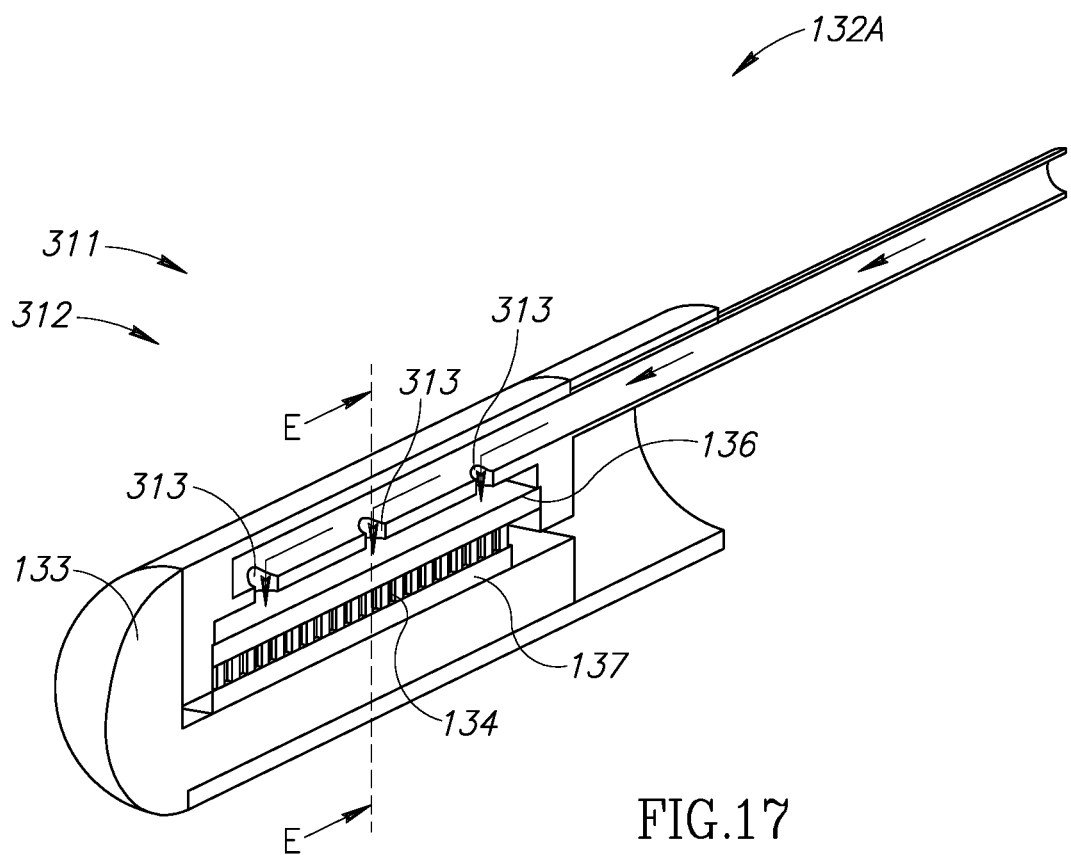
FIG. 17 is a longitudinal cross section of FIG. 1's catheter tip including a lengthwise thermoelectric module and a jet impingement module with three jet nozzles.
Figure 18:
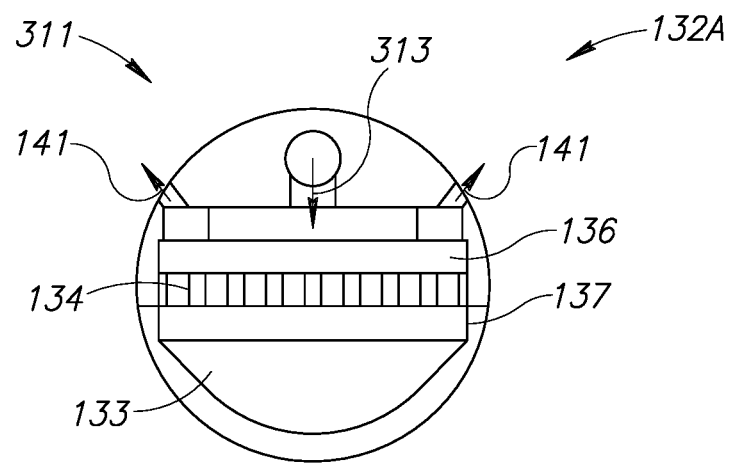
FIG. 18 is a transverse cross section of FIG. 17's catheter tip along line E-E in FIG. 17.

FIGS. 17 and 18 show an open irrigation catheter tip 132A including a jet impingement module 311 having a 1×3 array 312 of jet nozzles 313 for heat transfer from the same TEC Microsystems GmbH part number 1MD03-036-4 thermoelectric module 314 as FIG. 5's heat sink module 200. Each jet nozzle 313 has an internal jet nozzle diameter D=0.40 mm and an impingement height H=0.40 mm such that each jet nozzle 313 has a ratio D/H=1 within the range of 0.5<D/H<1.5. The TEC Microsystems GmbH part number 1MD03-036-4 has a 2.8 mm width, a 6.6 mm length and a near 20 mm² hot side footprint area.

The jet impingement module 311 requires three jet nozzles 313 to effectively conduct heat transfer along the length of thermoelectric module 314 as now explained with reference to the following calculations:

The jet impingement module 311 has three equi-distanced spaced jet nozzles 313 along its length such that each impingement zone radius R=1.15, adjacent jet nozzles 313 are spaced 2.3 mm apart and the two end jet nozzles 313 are each spaced 1.15 mm from the opposite ends of the thermoelectric module 314. Thus, the ratio R/D would be 1.15/0.40=2.75 which is in the range of the optimal value of R/D and therefore acceptable.

The jet impingement module 311 can employ requires a single jet nozzle 313 to effectively conduct heat transfer along the width of thermoelectric module 314 as now explained in the following second calculation:

The jet impingement module 311 has a single central jet nozzle 313 along its width such that its impingement zone radius R=2.8 mm/2=1.4 mm and the ratio R/D is 1.4/0.40=3.5 which is in the acceptable R/D range.

In the case of the jet impingement module 311, the Reynold number has a 410 value and the Prantel number has a 11 value such that according to equation (5) Nu=34 and according to equation (4) its heat transfer coefficient h=34× 0.58/0.4×10⁻³=49000 w/m²° C. As already defined, in jet impingement cooling Ah=Af and therefore according to equation (3), the jet impingement module 314 has a convection temperature difference Δt1:

$$\Delta t1 = \frac{Q}{h \times Ah} = \frac{7.5}{49000 \times 20 \times 10^{-6}} \cong 8° \text{ C.}$$

The thermoelectric module hot side 136 has a hot side temperature Thot=Tin+Δt1=5° C.+8° C.=13° C. such that the thermoelectric module cold side 137 has a cold side temperature Tcold=Thot−35° C.=13° C.−35° C.=−22° C. which is in the intended cryo-temperature range.

Figure 19:
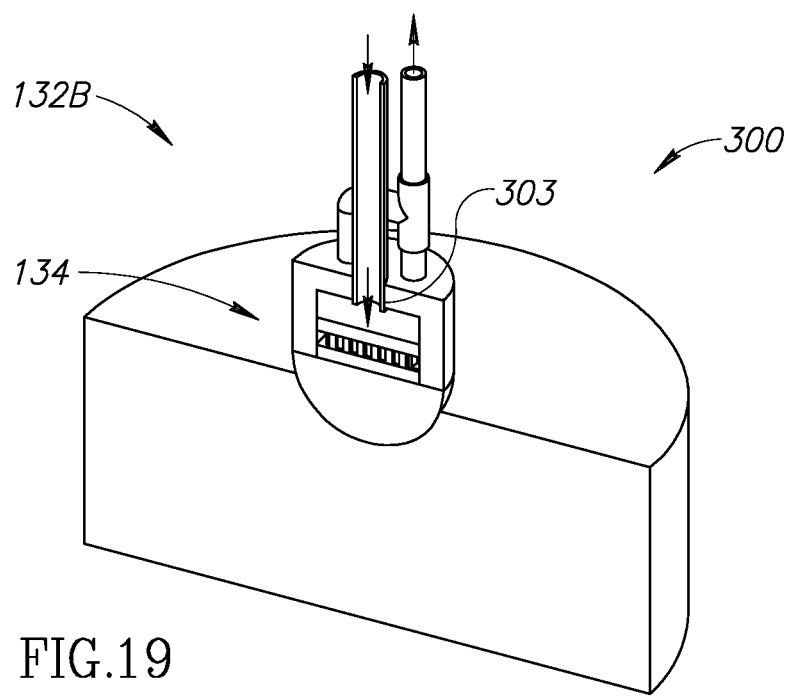
FIG. 19 is a perspective cross section of FIG. 3's catheter tip including a widthwise thermoelectric module and a jet impingement module with a single jet nozzle.

FIG. 19 shows a closed circuit catheter tip 132B having a widthwise thermoelectric module 134 and a jet impingement module 300 with a single jet nozzle 303.

Cryocatheter Designs

FIGS. 20 to 27 show different features of cryocatheters in accordance with the present invention. The features are not mutually exclusive and cryocatheters can include combinations of one or more features. Moreover, the cryocatheters can include lengthwise or widthwise thermoelectric modules. Also, the cryocatheters can include heat sink modules or jet impingement modules.

Figure 20:
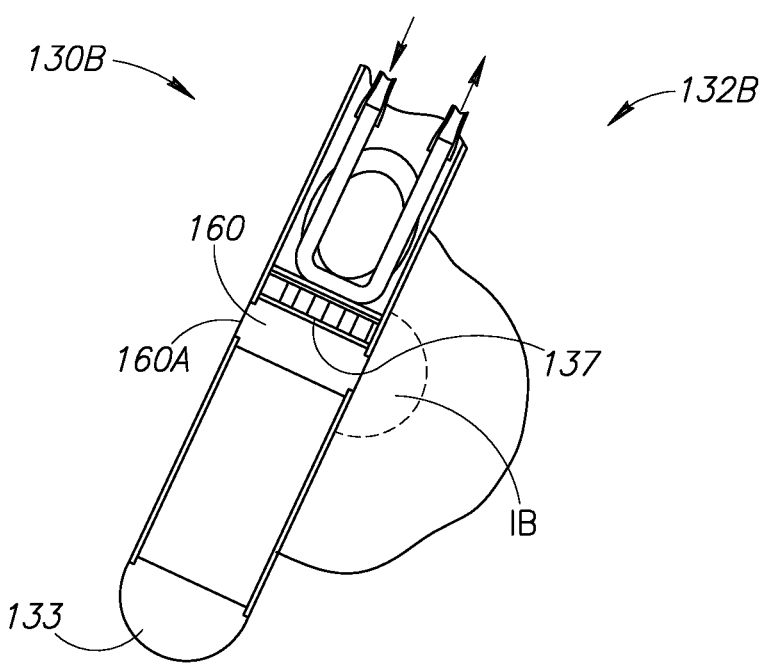
FIG. 20 is a longitudinal cross section of a FIG. 3's catheter tip for freezing a trailing section of the catheter tip.

FIG. 20 is a longitudinal cross section of a closed circuit cryocatheter 130B for freezing a trailing section of a catheter tip 132B for forming an ice ball IB deployed trailing its leading catheter dome 133. The cryocatheter 130B includes a metal plate 160 in high conductive thermal contact with the thermoelectric module cold side 137. The metal plate 160 has a peripheral cylindrical surface 160A for freezing human tissue in contact therewith. The length of the catheter tip 132B extending from the metal plate 160 to the catheter dome 133 is preferably made from non-highly heat conductive materials such as polyamide. The catheter dome 133 may be made from metal for clinical applications requiring electrical conductivity.

Figure 21:
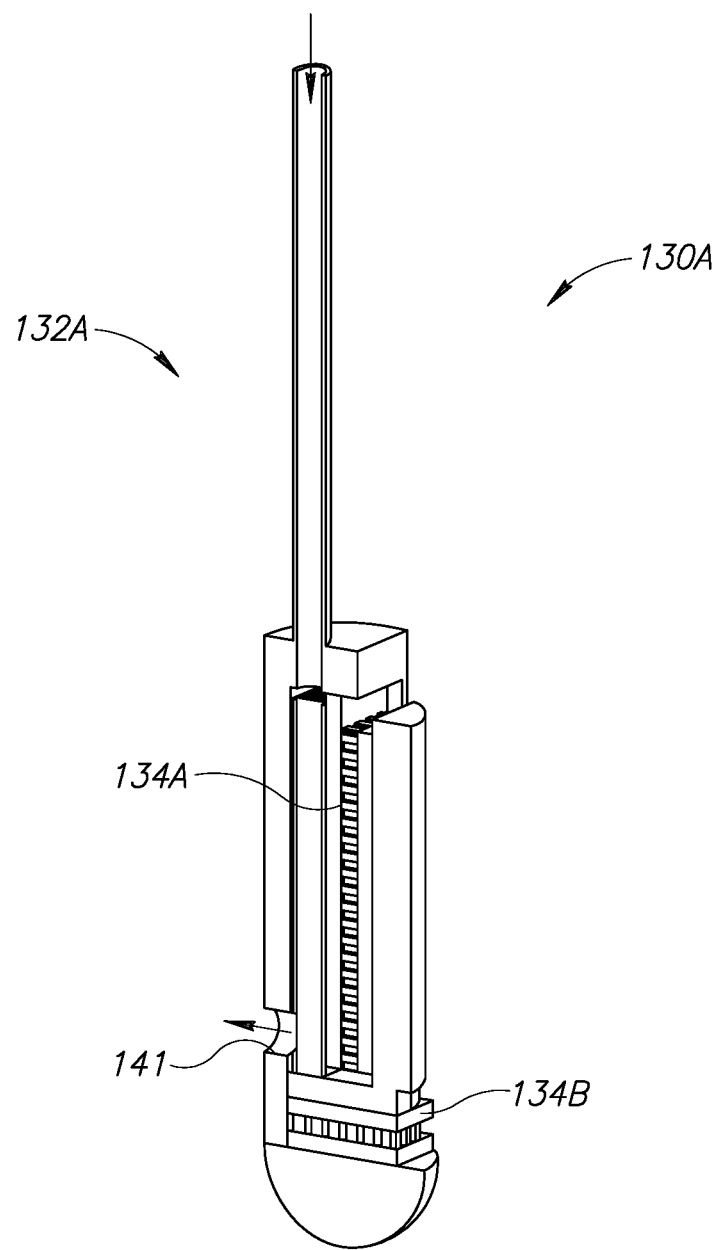
FIG. 21 is a longitudinal cross section of a FIG. 1's catheter tip including a lengthwise thermoelectric module and a widthwise thermoelectric module and a heat sink module.

FIG. 21 is a longitudinal cross section of an open irrigation cryocatheter 130A with a catheter tip 132A including a lengthwise thermoelectric module 134A and a widthwise thermoelectric module 134B and a heat exchange arrangement 138 for simultaneous heat transfer from both the thermoelectric modules 134A and 134B. The thermoelectric modules 134A and 134B can be considered to have a single hot side with a hot side footprint area equal to the sum of their individual hot side footprint areas.

Figures 22, 23:
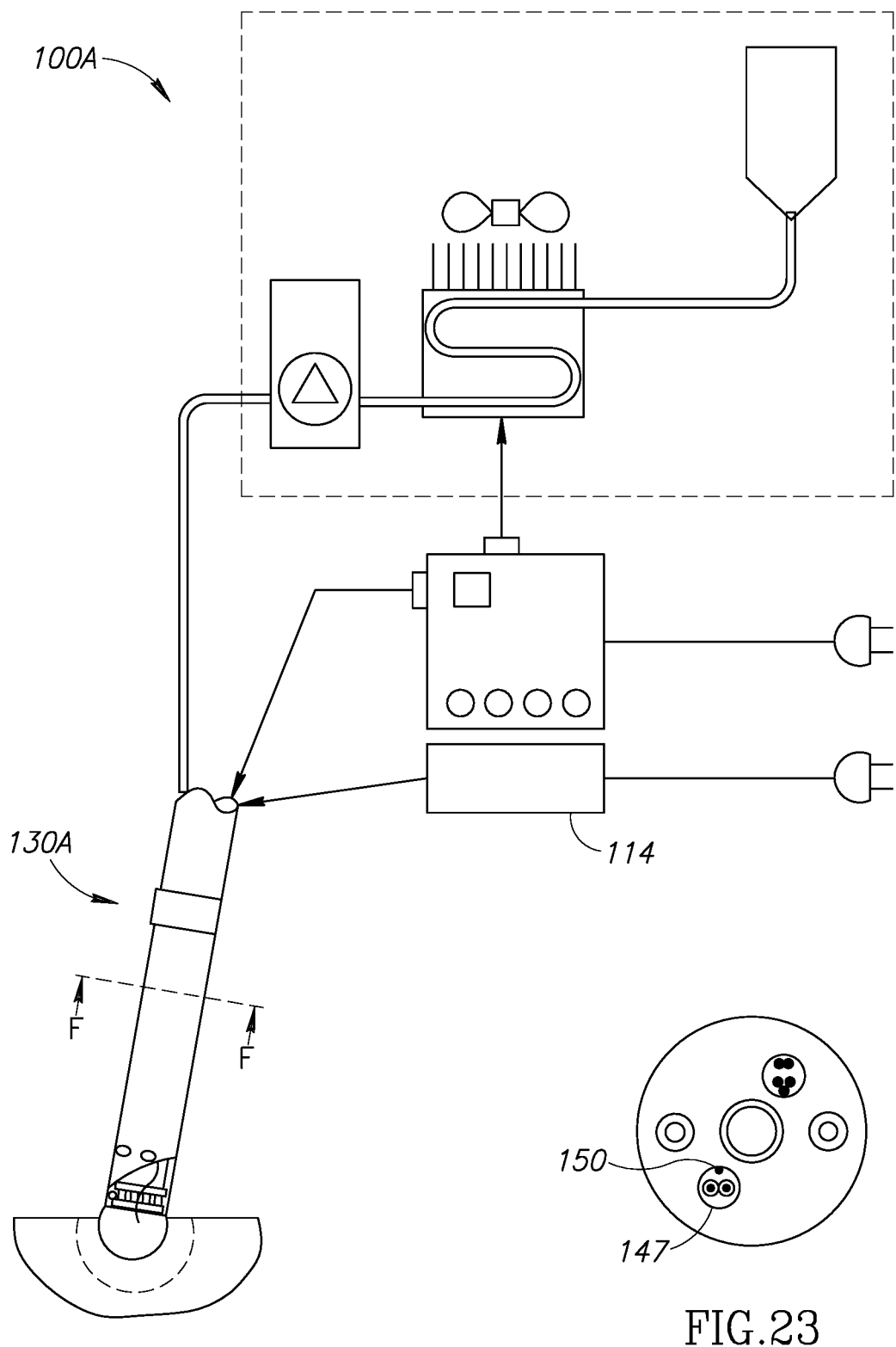
FIG. 22 is a block diagram of an open irrigation cryocatheter system including a cryocatheter and a RF ablator for RF ablation at a therapy site.
FIG. 23 is a transverse cross section of FIG. 22's catheter member along line F-F in FIG. 22.

FIGS. 22 and 23 show an open irrigation cryocatheter system 100A including an open irrigation cryocatheter 130A and a RF ablator 114 for RF ablation at a therapy site. The RF ablator 114 is connected to the dome 133 with a conductor wire 150.

Figures 24, 25:
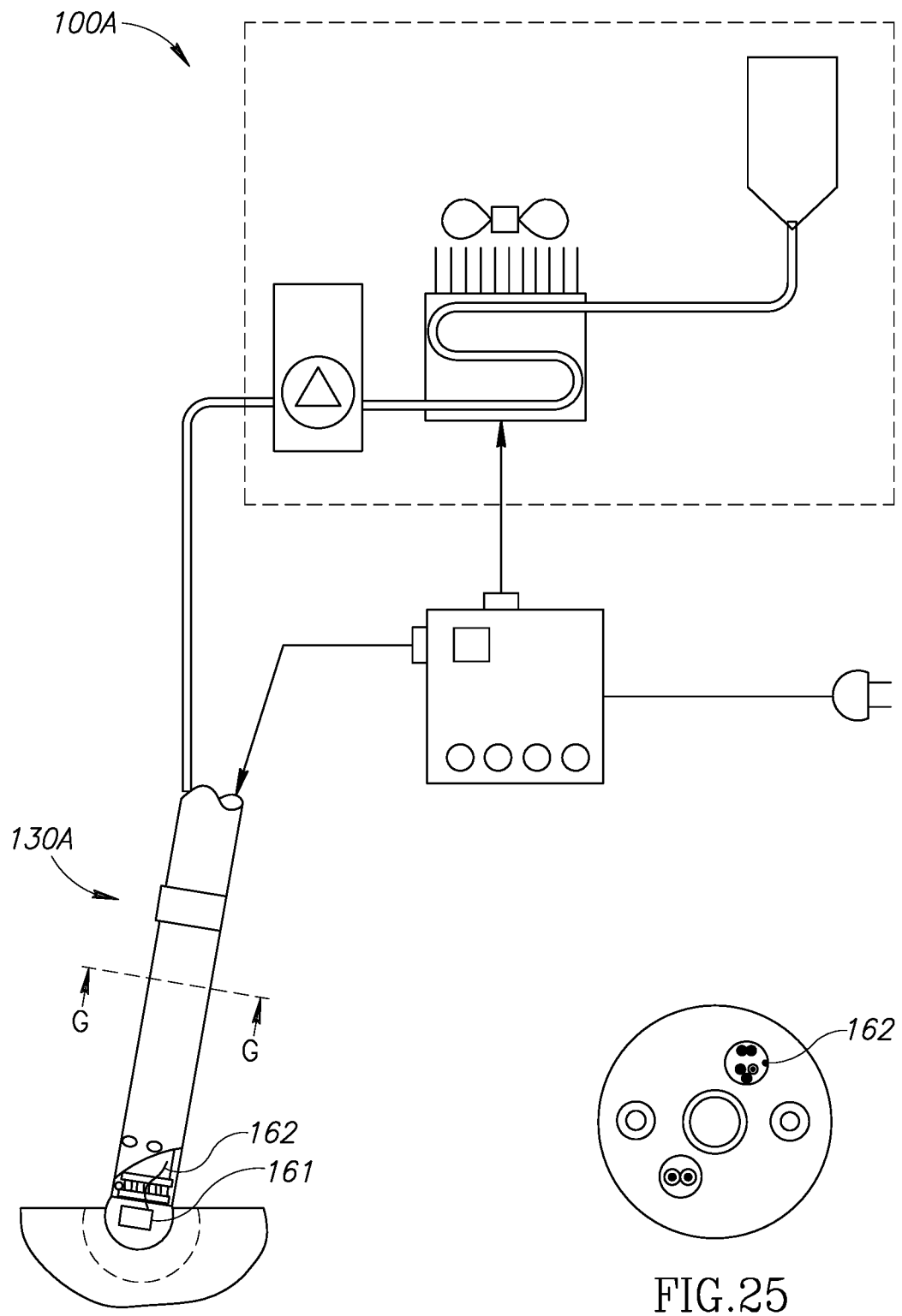
FIG. 24 is a block diagram of an open irrigation cryocatheter system including a cryocatheter having a catheter tip with a sensor.
FIG. 25 is a transverse cross section of FIG. 24's catheter member along line G-G in FIG. 24.

FIGS. 24 and 25 show an open irrigation cryocatheter system 100A including an open irrigation cryocatheter 130A having a catheter tip 132A with an acquisition device 161 for acquiring patient information at the therapy site. Exemplary acquisition devices 161 include inter alia a sensor for sensing a physiological parameter, a camera, and the like. Exemplary sensors include inter alia an ultrasound sensor, a pressure gauge, and the like. The controller 103 is connected to the acquisition device 161 by a signal wire 162.

Figures 26, 27:
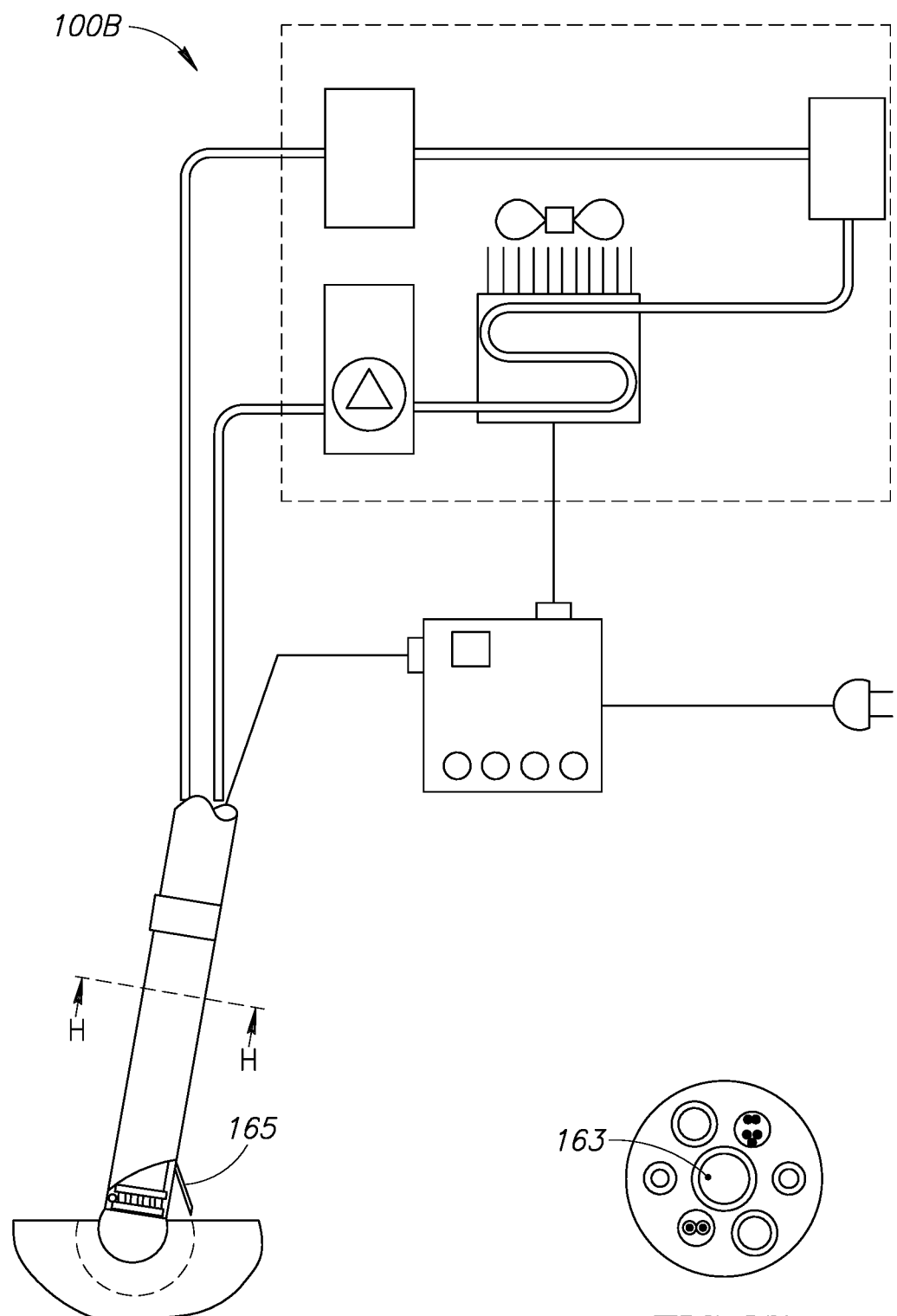
FIG. 26 is a longitudinal cross section of an open irrigation cryocatheter including a pair of vacant lumens for introduction of surgical tools at a therapy site.
FIG. 27 is a transverse cross section of FIG. 26's catheter member along line H-H in FIG. 26.

FIGS. 26 and 27 show a closed circuit cryocatheter system 100B including vacant lumens 163 for introduction of a surgical tool at a therapy site. Such surgical tools could be, for example, a biopsy needle 165 connected to an external suction pump.

Medical Procedures Employing an Ice Ball at a Cerebral Target Site

Figure 28:
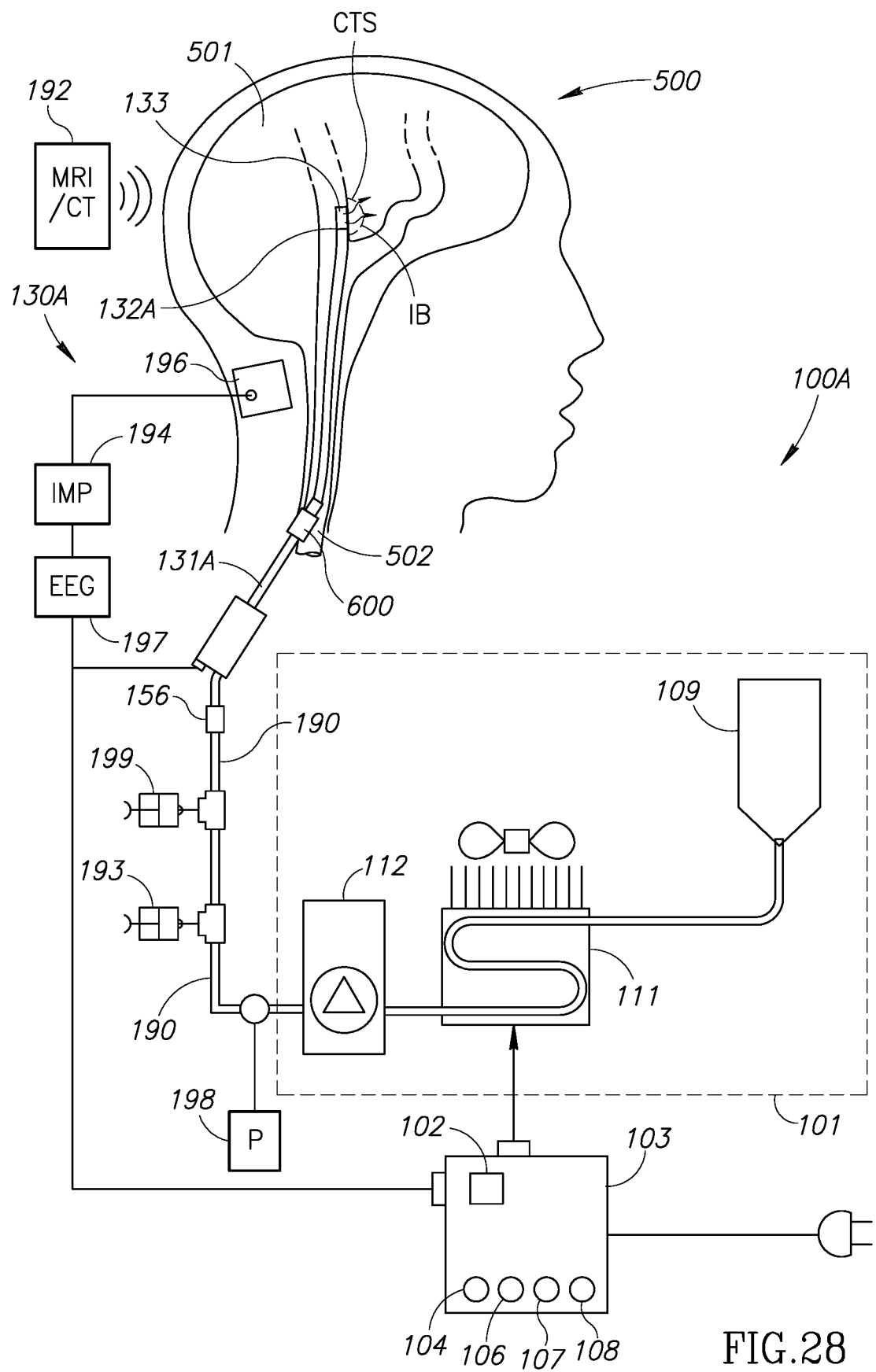
FIG. 28 is a combined pictorial view and block diagram of an open irrigation cryocatheter system for forming an ice ball at a cerebral site in accordance with the second aspect of the present invention.
Figure 29:
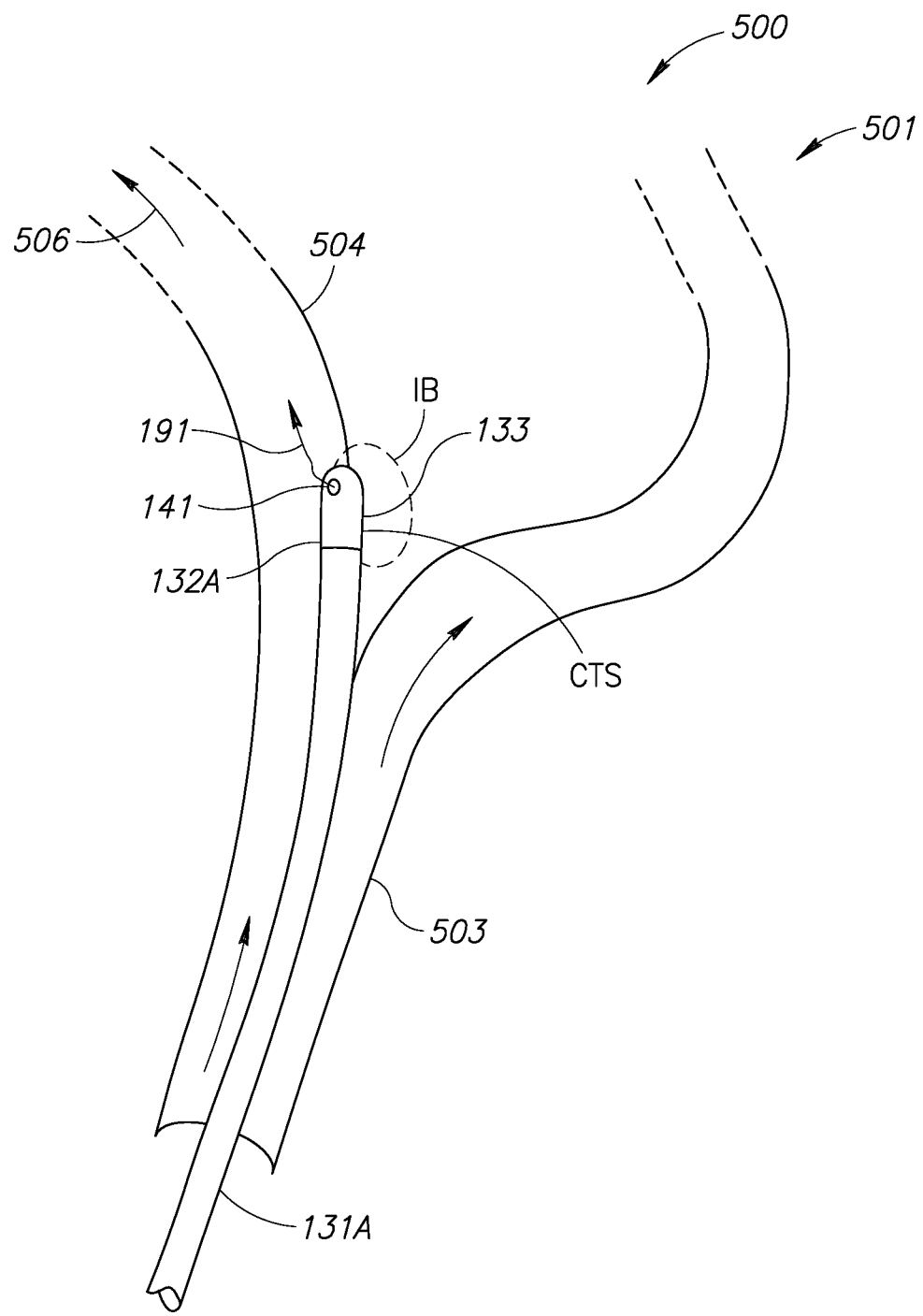
FIG. 29 is a close up view of a cryocatheter tip in an MCA area for generating an ice ball at a cerebral site.

FIGS. 28 and 29 show an open irrigation cryocatheter system 100A employing an ice ball IB for performing a medical procedure at a patient's cerebral target site CTS. The cerebral target site CTS is located in a brain 500's cerebral cortex 501 and is accessed through a patient's internal carotid 502. The cerebral target site CTS is located along a cerebral artery 503 having an arterial wall 504. The cerebral artery 503 has an arterial blood flow 506 which preferably remains uniform during the formation of the ice ball IB in the arterial wall 504. The cyrocatheter 130A is inserted into the internal carotid 502 via a sheath 600 acting as an access port.

The cryocatheter system 100A necessarily employs a bio-compatible liquid for cooling purposes. The bio-compatible liquid is preferably 0.9% NaCl saline, and the like. The cryocatheter system 100A includes an irrigation tube 190 for feeding the open irrigation catheter 130 from the external liquid coolant source 101. The bio-compatible liquid exits the catheter tip 132A through the irrigation holes 141 to join the arterial blood flow 504 as an irrigation flow 191.

Navigation of a catheter tip 132A to a cerebral target site CTS is achieved by a radiology imaging system 192. Suitable imaging systems include inter alia MRI, CT, X-ray (Fluoroscopy), and the like. Such imaging systems 192 can be assisted by the use of a contrast agent to be injected into the irrigation tube 190 by a contrast agent syringe 193. The contrast agent syringe 193 can be a manual syringe or a syringe pump. The contrast agent also exits the catheter tip 132A through the irrigation holes 141 with the irrigation flow 191 to join the arterial blood flow 506.

Contact of the catheter dome 133 at a cerebral target site CTS is detected by an impedance measurement device 194 connected to the catheter dome 133 and a counter electrode 196 connected to the patient's skin typically at his scalp. When the metallic catheter dome 133 touches the arterial wall 504, impedance increases relative to the impedance when the metallic catheter dome 133 is immersed in blood. An ElectroEncephaloGraphy (EEG) measurement device 197 is also preferably connected to the catheter dome 133 and the counter electrode 196. The impedance measurement device 194 and the EEG measurement device 197 are preferably connected to the controller 103. The impedance measurement device 194 and the EEG measurement device 197 can be preferably integrated in a single electrical device.

The irrigation tube 190 includes a pressure monitor 198 for detecting an increase in back pressure which can be indicative of artery blockage in the cerebral artery 503 at the cerebral target site CTS due to the formation of the ice ball IB on its arterial wall 504.

The open irrigation cryocatheter system 100A can also include a blood clotting agent syringe 199 for injecting a blood clotting agent at a stroke hemorrhage site. Typical medications include antihypertensive drugs (such as beta-blockers) and blood-coagulators for accelerating local clotting. The blood clotting agent syringe 199 can be a manual syringe or a syringe pump. The blood clotting agent also exits the catheter tip 132A through the irrigation holes 141 with the irrigation flow 191.

Figure 30:
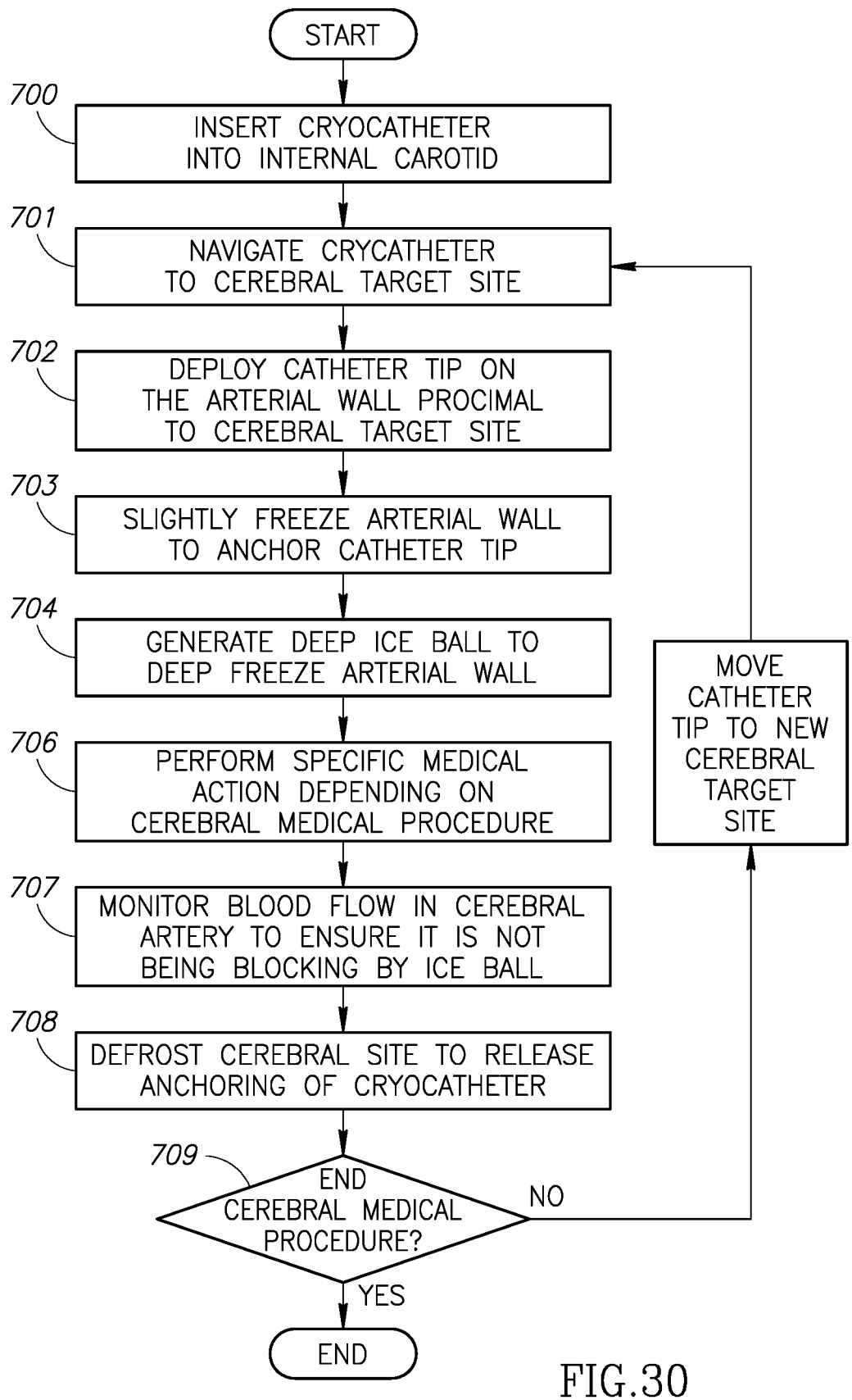
FIG. 30 is a flow chart of a cerebral medical procedure using a cryocatheter of the present invention to generate a local ice ball.
Figure 31:
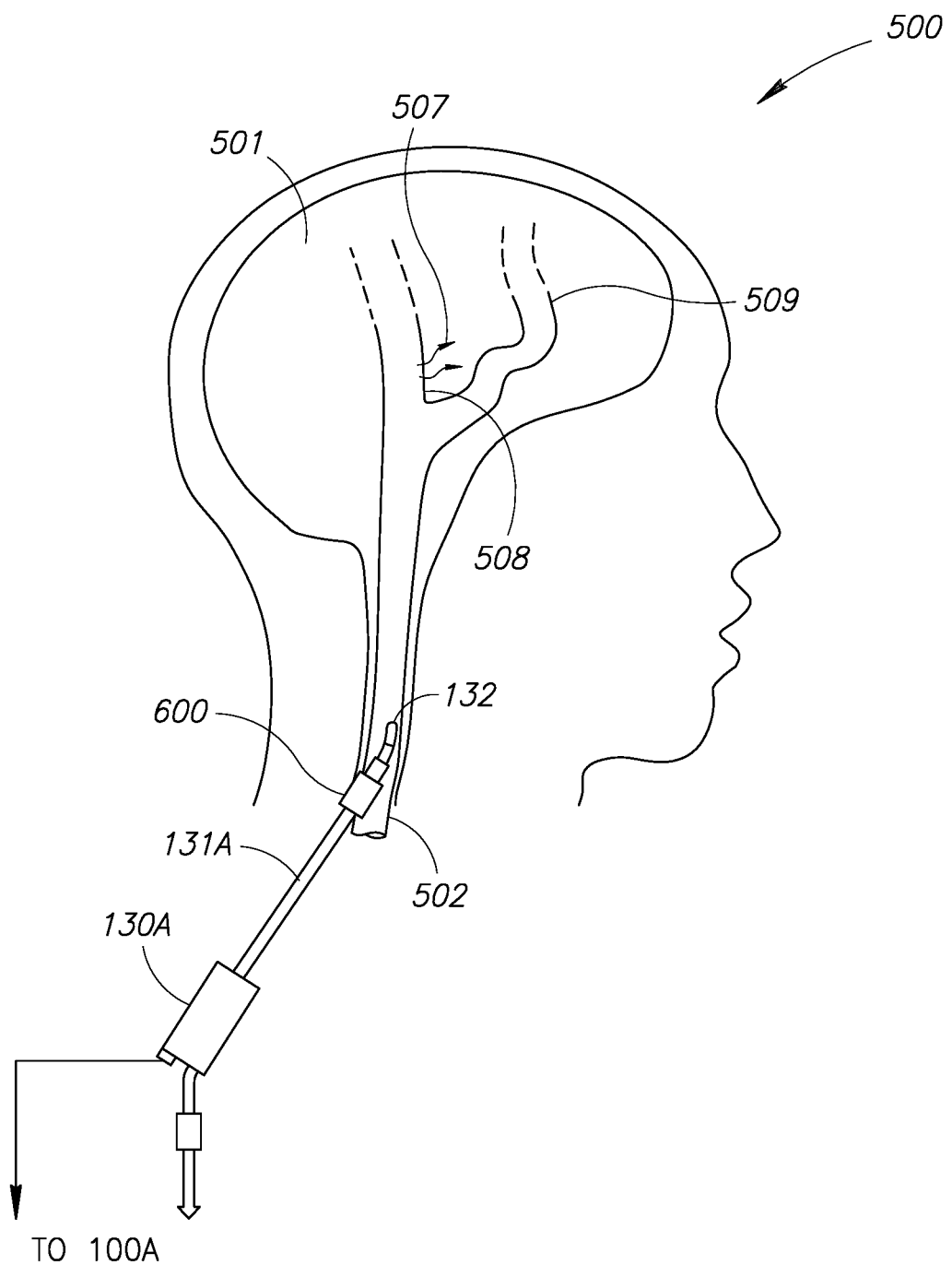
FIG. 31 shows insertion of a cryocatheter into an internal carotid for stopping bleeding at a stroke hemorrhage site.

FIG. 30 shows the cerebral medical procedures include inter alia following steps:
Step 700 Insert cryocatheter into an internal carotid
Step 701 Navigate cryocatheter to cerebral target site
Step 702 Deploy catheter tip on arterial wall proximal to the cerebral target site
Step 703 Operate cryocatheter to generate a shallow ice ball to slightly freeze the arterial wall to anchor catheter tip
Step 704 Operate cryocatheter to generate a deep ice ball to deep freeze arterial wall
Step 706 Perform a specific medical action depending on a cerebral medical procedure
Step 707 Monitor blood flow in the cerebral artery to ensure the ice ball is not blocking same
Step 708 Defrost the cerebral target site to release anchoring of the cryocatheter tip
Step 709 Determine whether cerebral medical procedure has ended. In the affirmative, withdraw the cyrocatheter from the patient. In the negative, continue the cerebral medical procedure from step 701
Medical Procedure for Stopping Bleeding at a Stroke Hemorrhage Site FIGS. 31 to 38 show the steps for stopping bleeding 507 at a stroke hemorrhage site 508 constituting a cerebral target site CTS in the Middle Cerebral Artery (MCA) region 509 as follows:

FIG. 31 shows insertion of a catheter tip 132A into an internal carotid. The flexible catheter member 131 is inserted through a sheath 600 to the brain common carotid and then pushed therealong in this example to the internal carotid 502.

Figure 32:
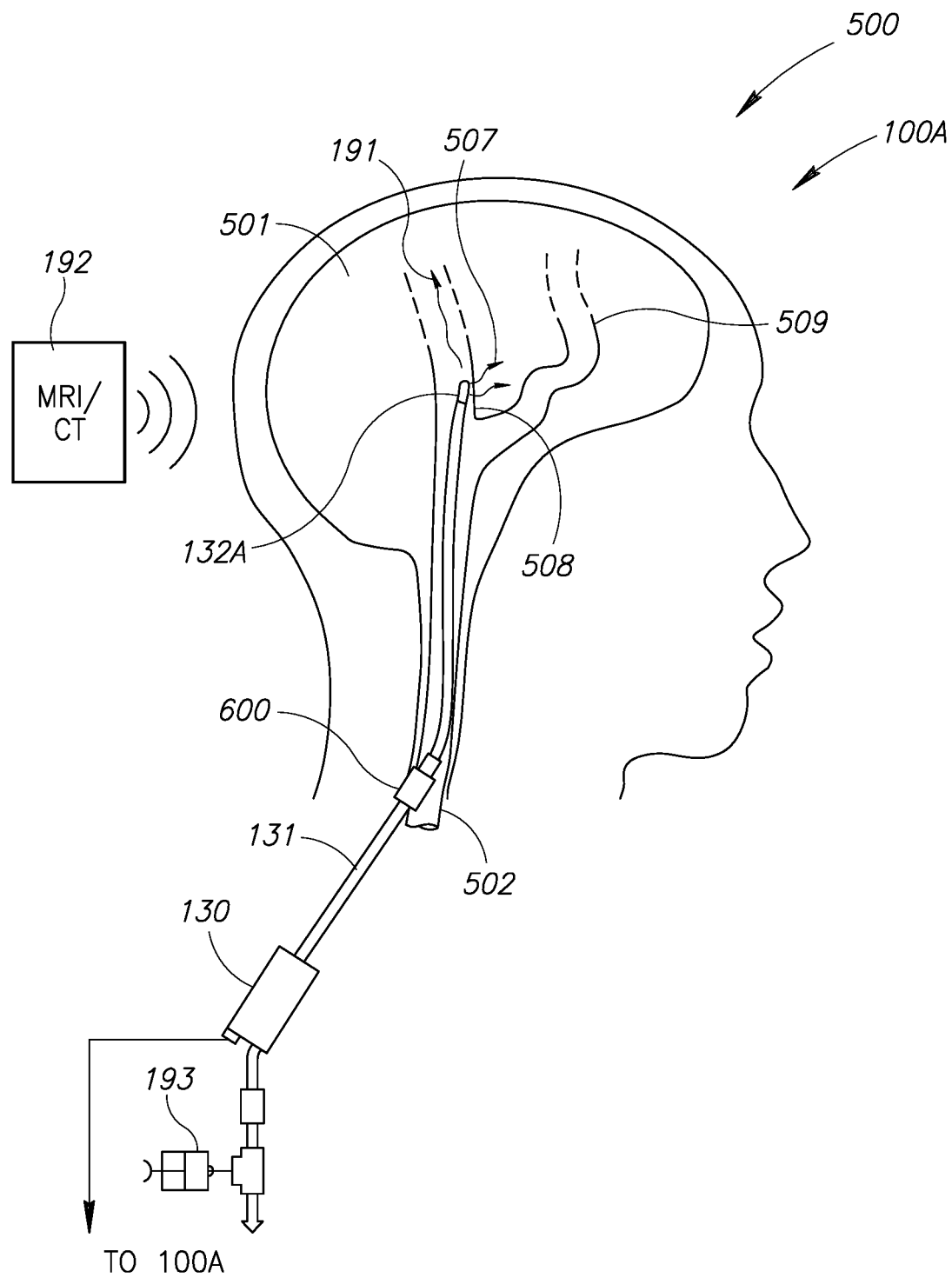
FIG. 32 shows navigation of the cryocatheter to the bleeding rupture of the stroke hemorrhage site.

FIG. 32 shows the use of a MRI radiology imaging system 192 to navigate the catheter tip 132A to the cerebral target site CTS. The preferred positioning accuracy along the arterial wall 504 is about +/−1 millimeter. A physician may inject some contrast agent from the syringe 193 into the irrigation tube 190 to discharge through the irrigation holes 141 as part of the irrigation flow 191 for radiology inspection to monitor the location of the catheter tip 142A.

Figure 33:
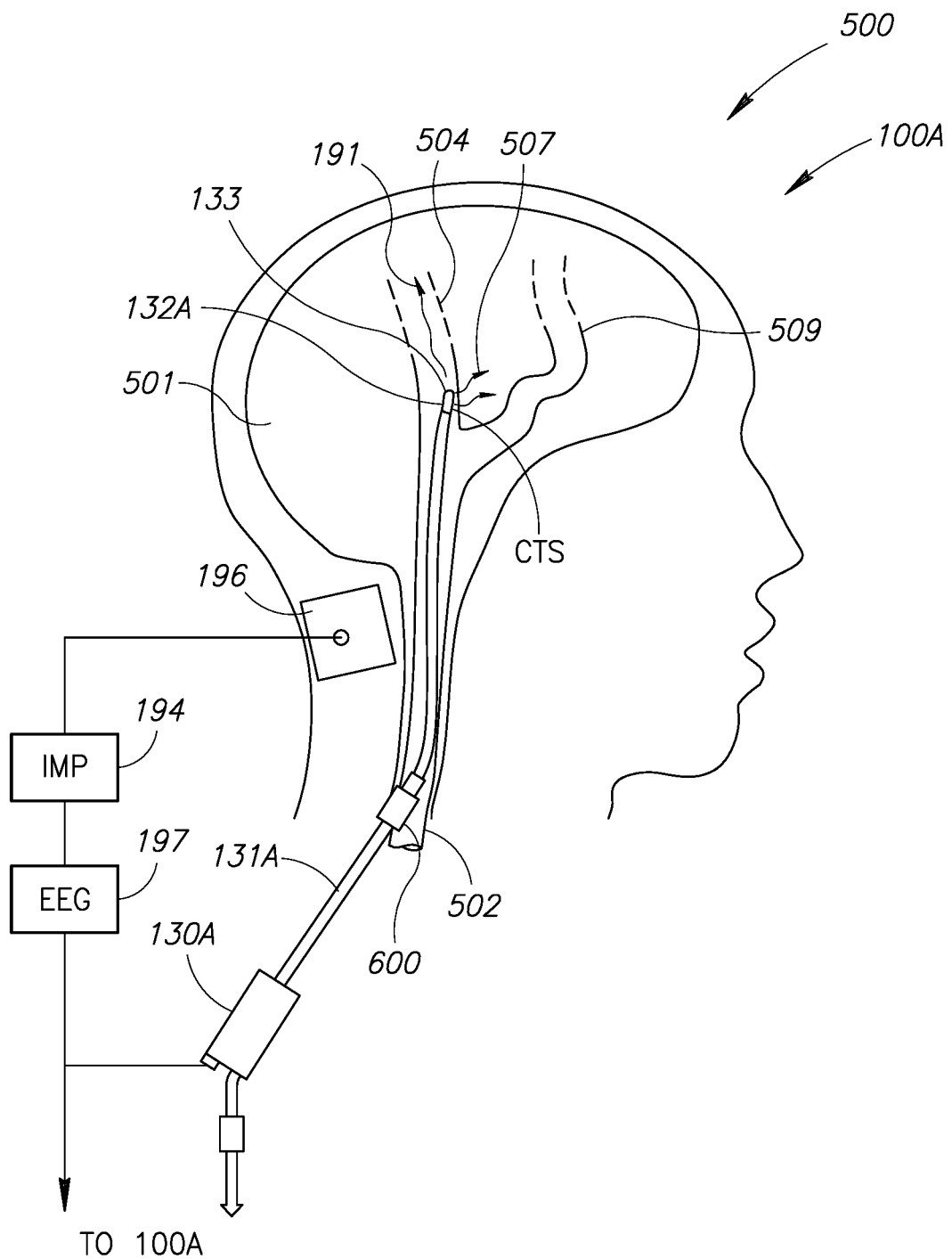
FIG. 33 shows deploying the cryocatheter tip at an arterial wall proximal to the bleeding rupture.

FIG. 33 shows deployment of the cryocatheter tip 132A on the arterial wall 504 proximal to the stroke hemorrhage site 508. The impedance measurement device 194 measures the bio-impedance between the catheter dome 133 and the counter electrode 196. When the catheter dome 133 touches the arterial wall 504, the bio-impedances increases relative to the bio-impedance of the catheter dome 133 immersed in blood. Also, the EEG measurement device 197 simultaneously measures an increased EEG signal level relative to the previous "not touching" position.

Figure 34:
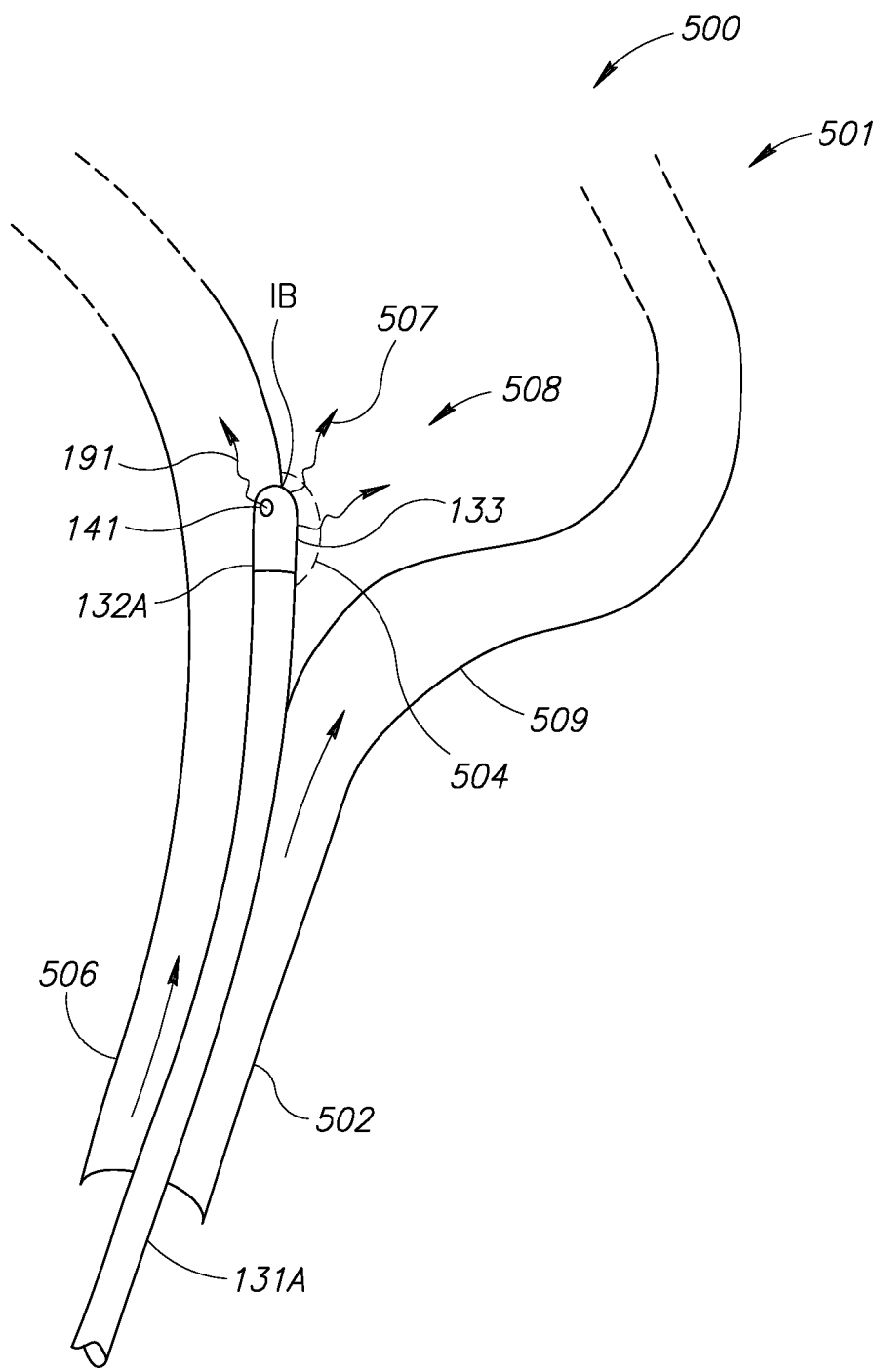
FIG. 34 shows operating the cryocatheter to generate a shallow ice ball to slightly freeze the arterial wall for anchoring the cryocatheter tip at the bleeding rupture.

FIG. 34 shows operating the cryocatheter 130A to cool the catheter tip 132A to a temperature range of about −10° C. to −20° C. for a relatively short time duration of 1 to 2 minutes to generate a shallow ice ball IB to slightly freeze the arterial wall 504. The cryocatheter 130A generates a shallow ice ball IB of about 0.5 to 1.0 millimeter depth into the arterial wall 504 and anchors the cryocatheter tip 132 at the stroke hemorrhage site 508. The imaging system 192 can be employed for ensuring the catheter tip 132A is placed at the stroke hemorrhage site 508 and is stable.

Figure 35:
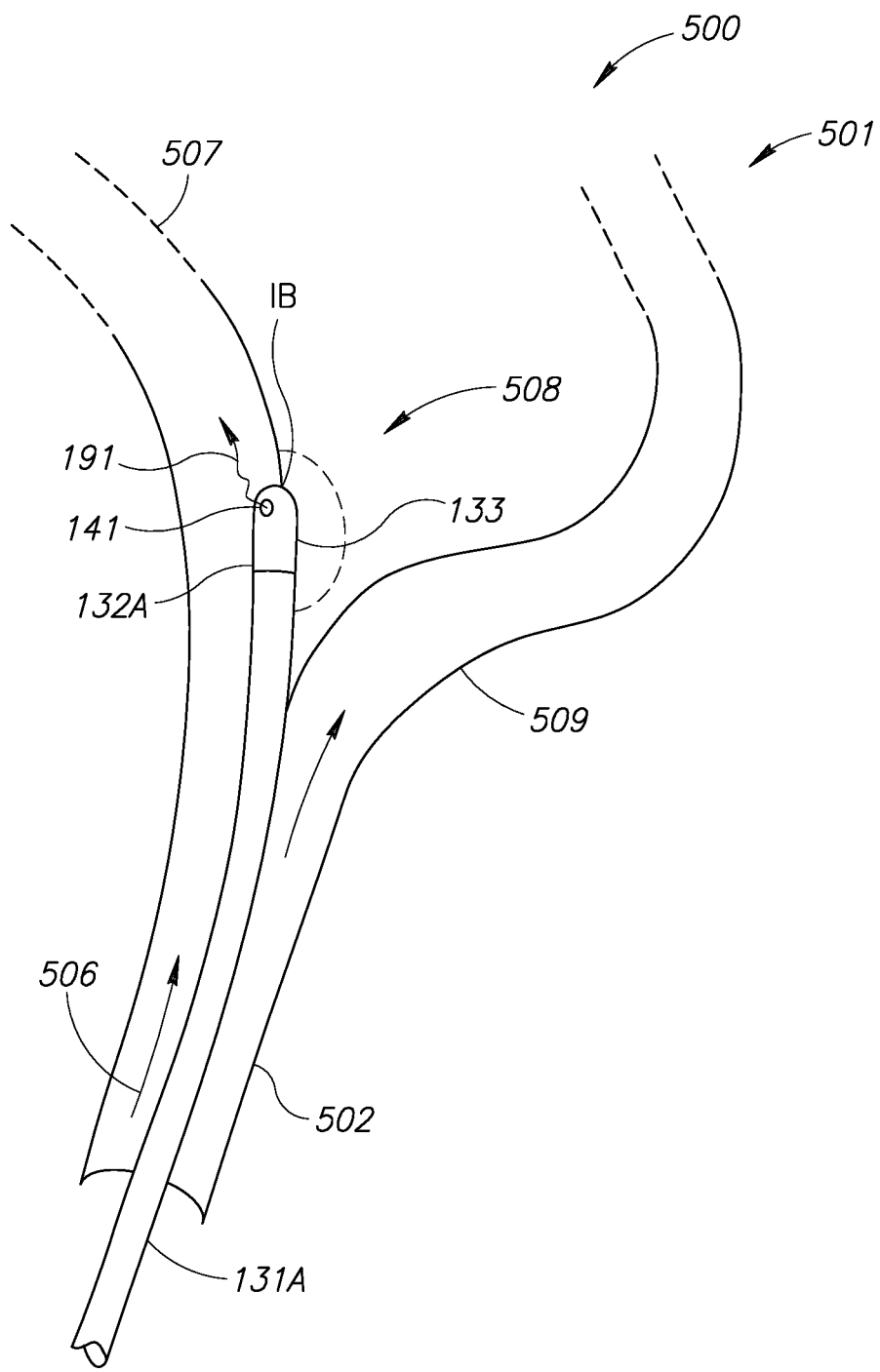
FIG. 35 shows operating the cryocatheter to generate a deep ice ball to deep freeze the arterial wall at the bleeding rupture to stop bleeding.

FIG. 35 shows operating the cryocatheter system 100 to cool the catheter tip 132 to a cryotemperature from −10° C. to −30° C. and preferably in the range of −25° C. to −30° C. for a time duration from between 20 minutes to 120 minutes to generate a deep ice ball IB with a typical radius of about 3-4 millimeter to deep freeze the arterial wall 507 to stop bleeding.

Figure 36:
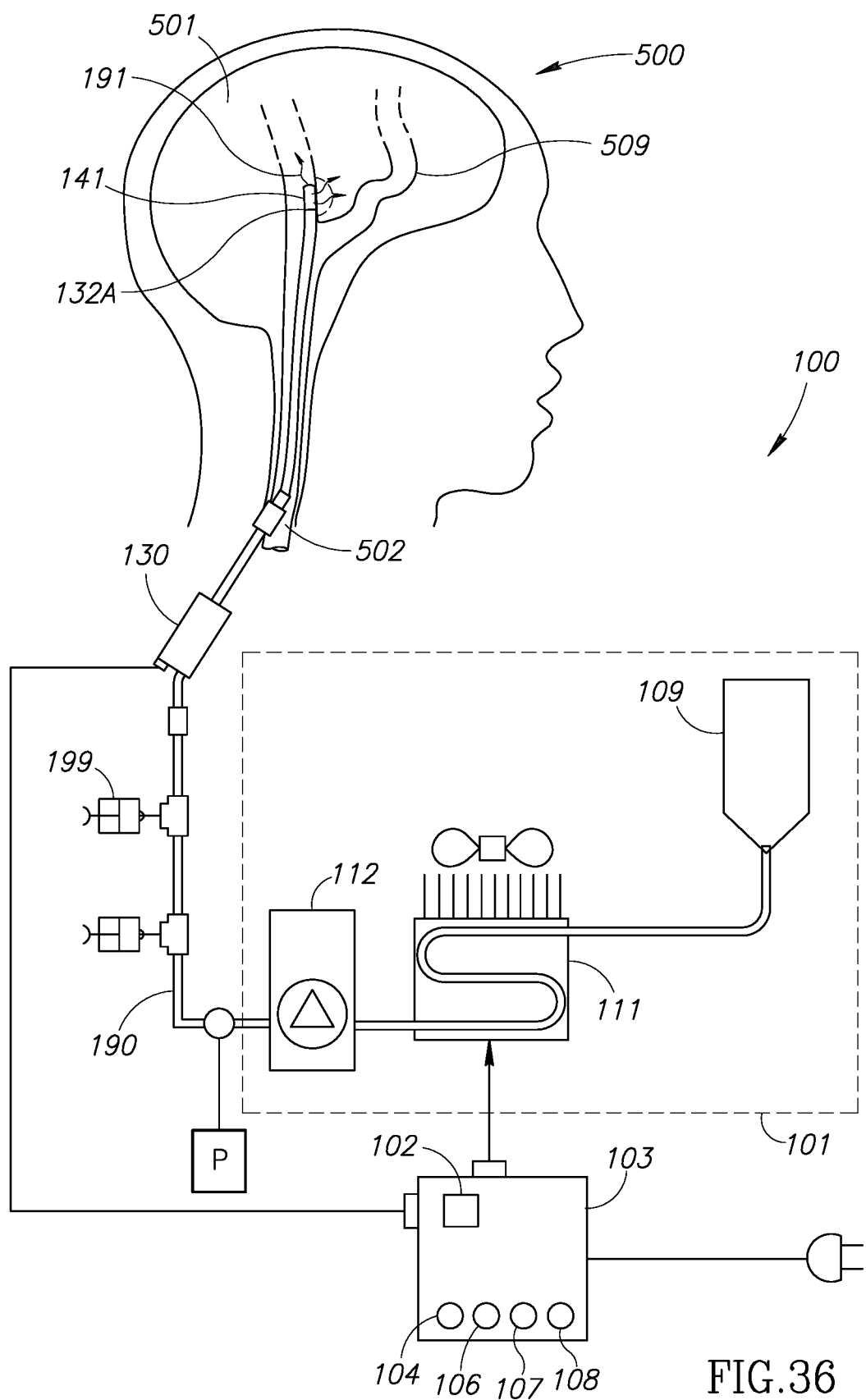
FIG. 36 shows injecting a blood clotting drug into an irrigation line for accelerating local clotting at the bleeding rupture.

FIG. 36 shows injecting a blood clotting drug from the syringe 199 into the irrigation tube 190. The drug is discharged directly to the stroke hemorrhage site 508 via the irrigation holes 141 into the irrigation flow 191. Such drug delivery directly to the stroke hemorrhage site 508 typically affords administering a smaller dosage compared with a common IV systemic injection.

Figure 37:
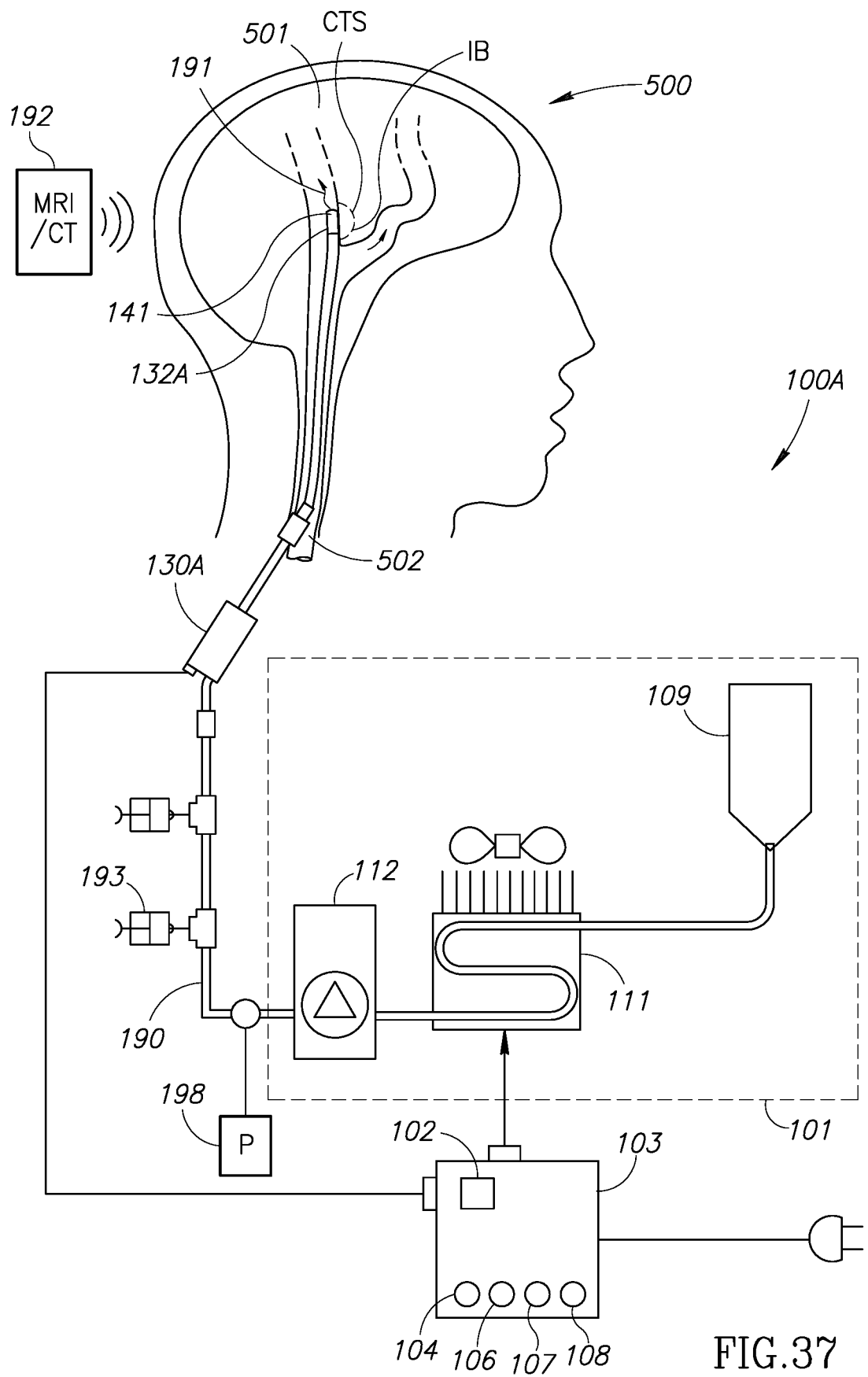
FIG. 37 shows monitoring blood flow in a treated artery to verify it is not being blocked by an ice ball protruding from an arterial wall.

FIG. 37 shows monitoring the arterial blood flow 506 in the cerebral artery 503 to verify it is not being blocked by the ice ball IB formed in the arterial wall 504. Monitoring of the arterial blood flow 506 can be achieved by one of two alternative monitoring modes. First, injecting contrast agent from the contrast agent syringe 193 to the irrigation tube 190 for discharge at the stroke hemorrhage site 508 through the irrigation holes 141 for radiology inspection using the radiology imaging system 192. And second, the pressure monitor 198 provides an indication for artery blockage at the stroke hemorrhage site 508 in the case of an increase in back pressure in the irrigation tube 190.

Figure 38:
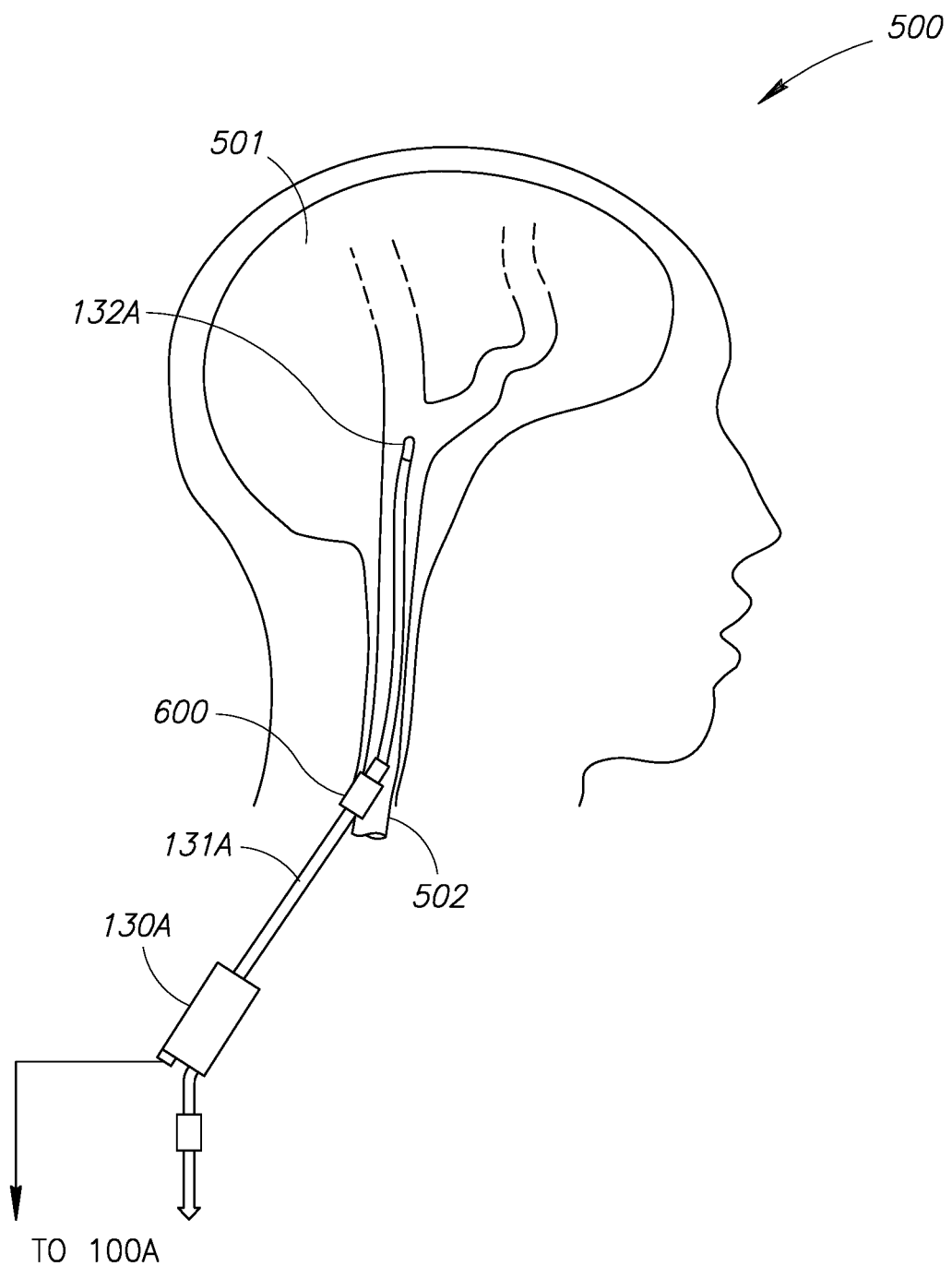
FIG. 38 shows defrosting the arterial wall to release the anchoring of the cryocatheter tip.

FIG. 38 shows defrosting the cerebral target site CTS by operating the controller 103's DEFROST control 107 for defrosting the catheter tip 132A until the temperature of the catheter dome 133 reaches a value of about +10° C. After releasing the anchoring of the catheter tip 132A, the cryocatheter 130A can be pulled back along its insertion path and withdrawn from the sheath 600. Alternatively, the cryocatheter 130A can be deployed at another stroke hemorrhage site for stopping bleeding thereat in the same manner.

In the case of a closed circuit cryocatheter system 100B, a contrasting agent and a blood clotting drug can be injected through a separate micro-catheter introduced proximate to the cerebral target site.

Medical Procedure for Mapping Cerebral Electrical Disorder Locations

FIGS. 39 to 46 show the steps for mapping cerebral electrical disorders locations at investigation locations 511 each constituting a cerebral target site CTS in the Middle Cerebral Artery (MCA) region 509. The steps for mapping the cerebral electrical disorder locations are similar as the aforesaid steps for stopping bleeding at a stroke hemorrhage site. Mapping cerebral electrical disorder locations additionally requires three steps as follows:

measuring an EEG signal at an investigation location before deep freezing an arterial wall for use as a reference EEG signal, the reference EEG signal including an electrical disorder signal, measuring an EEG signal at the investigation location pursuant to deep freezing the arterial wall for comparison to the reference EEG signal, and comparing the EEG signal pair to determine whether the electrical disorder signal in the reference EEG signal remains in the EEG signal after deep ice ball generation, and in the affirmative, thereby indicating the investigation location is not the source of the electrical disorder signal.

Mapping cerebral electrical disorder locations is to some extent a matter of trial and error and it typically takes several investigations to accurately locate cerebral electrical disorder locations.

Figure 39:
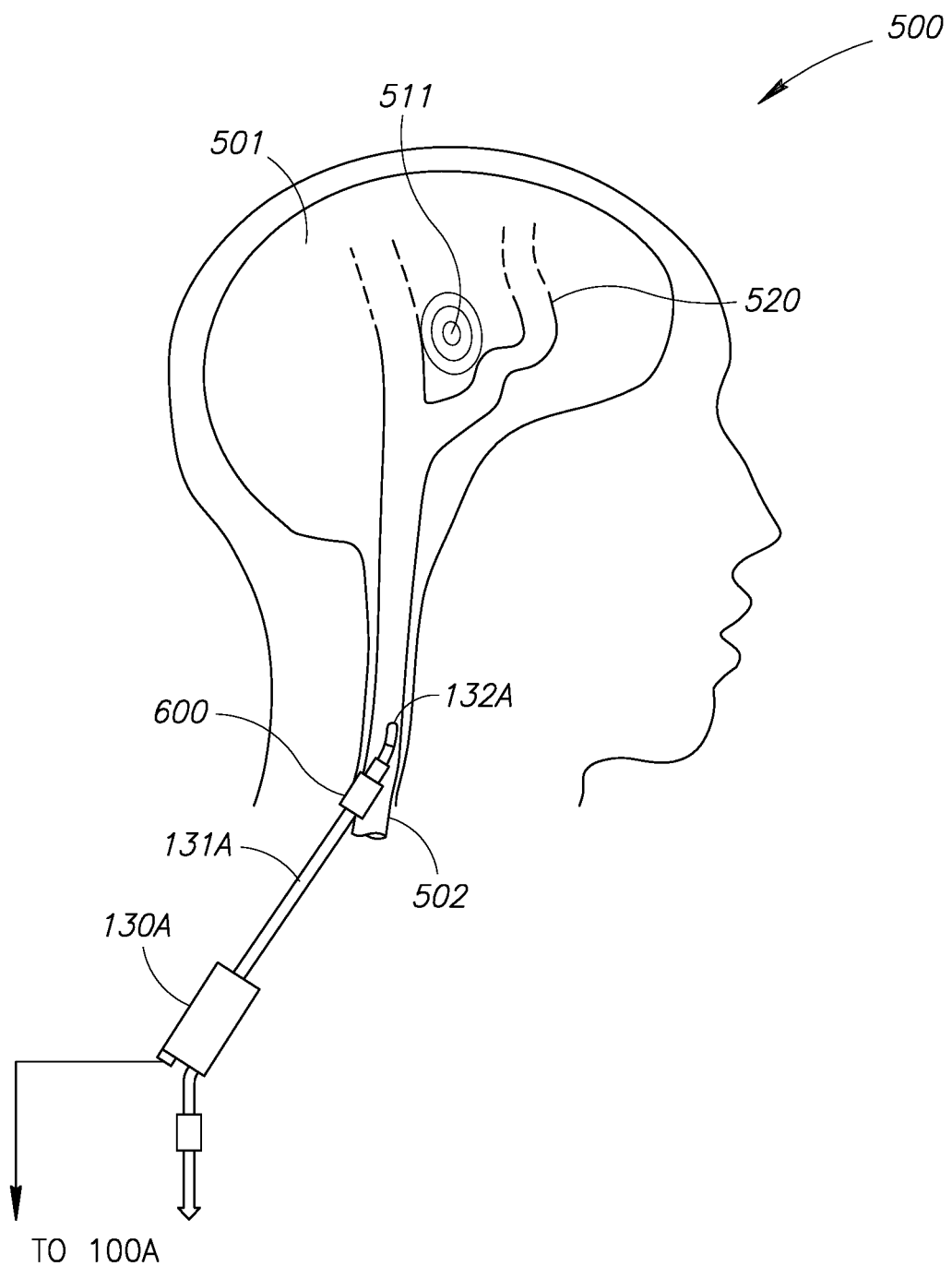
FIG. 39 shows insertion of a cryocatheter tip into an internal carotid for mapping cerebral electrical disorder locations.

FIG. 39 shows insertion of a catheter tip 132A into an internal carotid 502. The flexible catheter member 131 is inserted through a sheath 600 to the brain common carotid and then pushed therealong in this example to the internal carotid 502 towards an investigation location 511.

Figure 40:
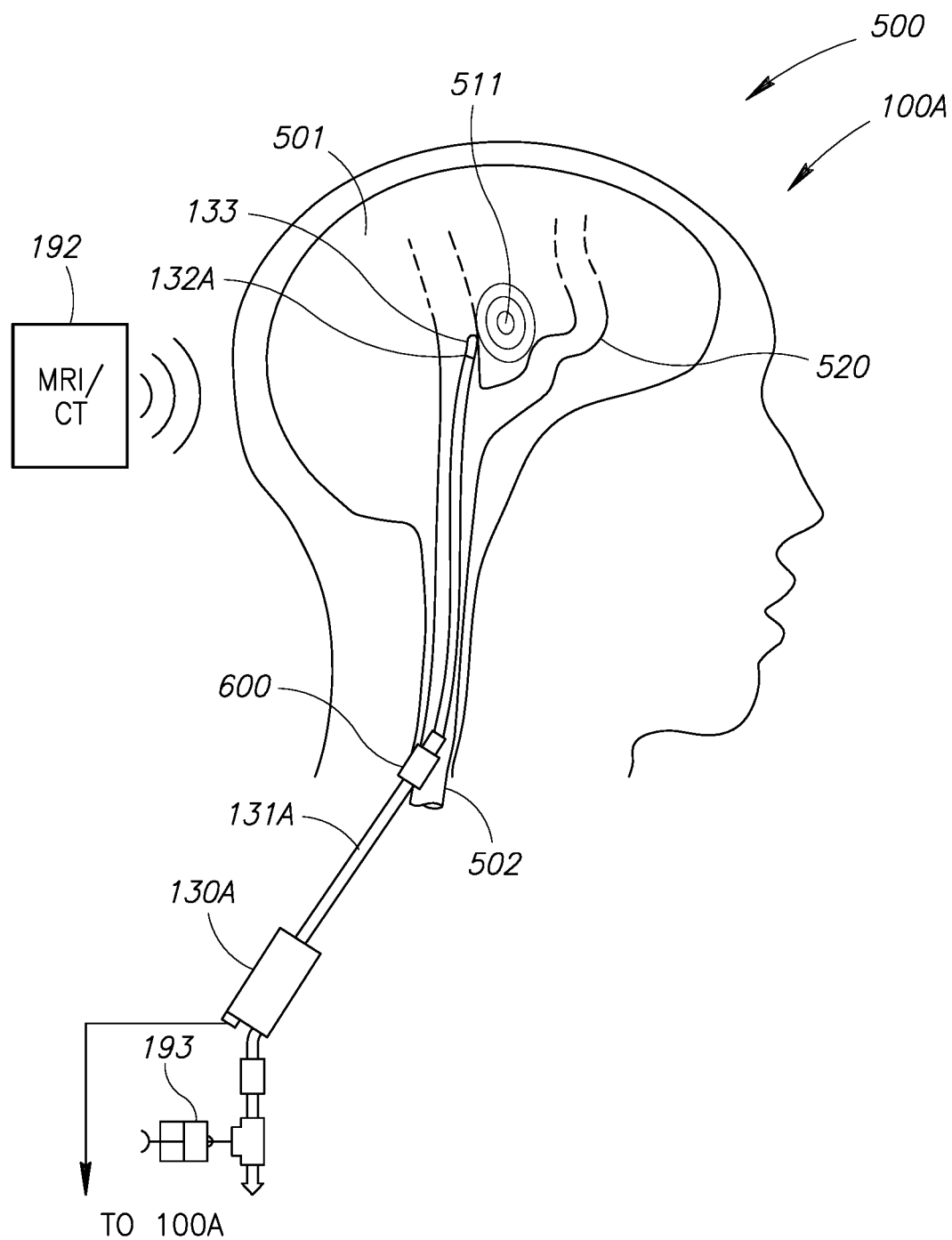
FIG. 40 shows navigation of the cryocatheter tip towards an investigation location.

FIG. 40 shows the use of a MRI radiology imaging system 192 to navigate the catheter tip 132A to an investigation location 511. The preferred positioning accuracy along the arterial wall 504 is about +/−1 millimeter. A physician may inject some contrast agent from the syringe 193 into the irrigation tube 190 to discharge through the irrigation holes 141 as part of the irrigation flow 191 for radiology inspection to monitor the location of the catheter tip 132A.

Figure 41:
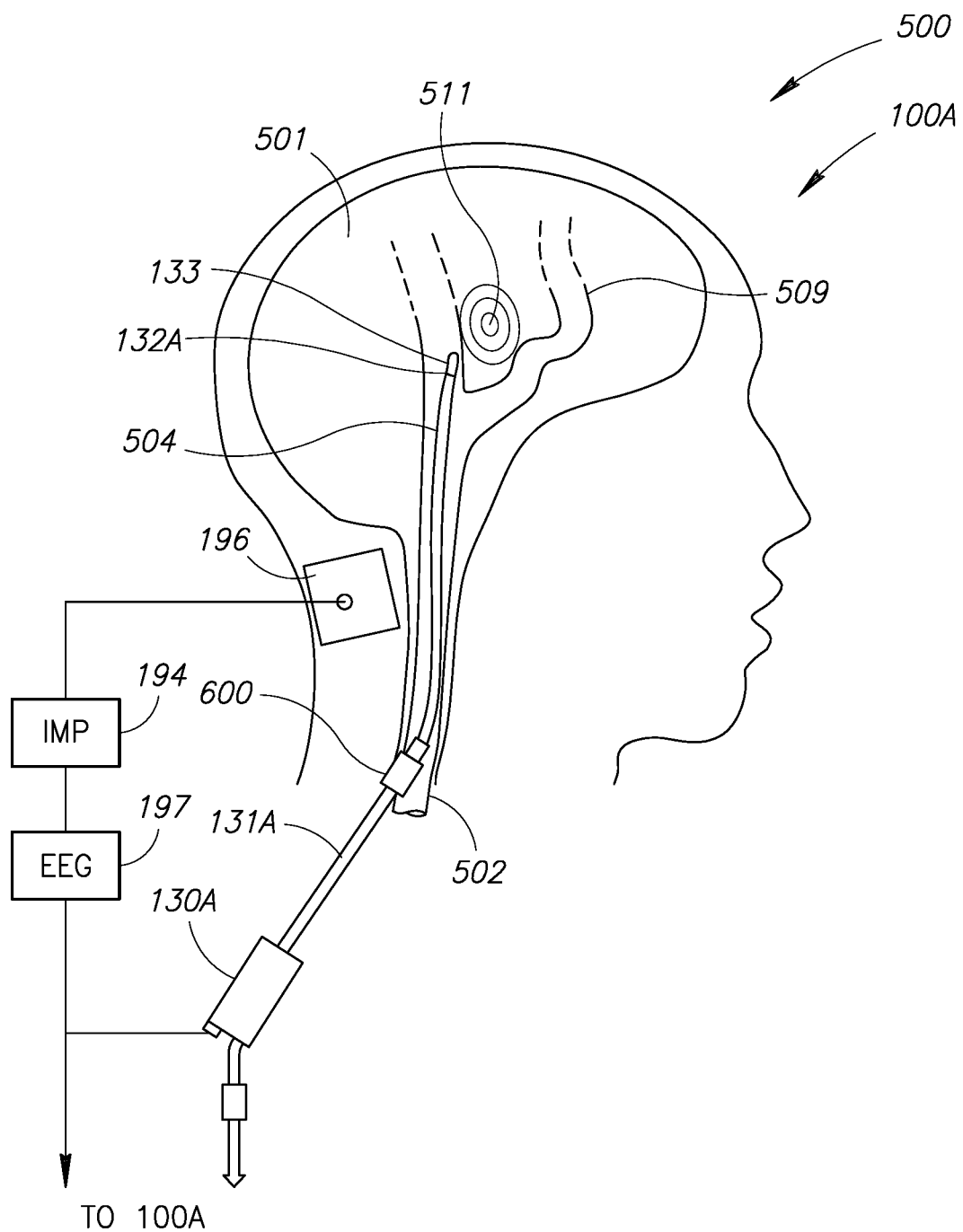
FIG. 41 shows deployment of the cryocatheter tip at an arterial wall proximal to an investigation location.

FIG. 41 shows deployment of the cryocatheter tip 132A on the arterial wall 504 proximal to the investigation location 511. The impedance measurement device 194 measures the bio-impedance between the catheter dome 133 and the counter electrode 196. When the catheter dome 133 touches the arterial wall 504, the bio-impedances increases relative to the bio-impedance of the catheter dome 133 immersed in blood. The EEG measurement device 197 measures an EEG signal level for use as a reference EEG signal.

Figure 42:
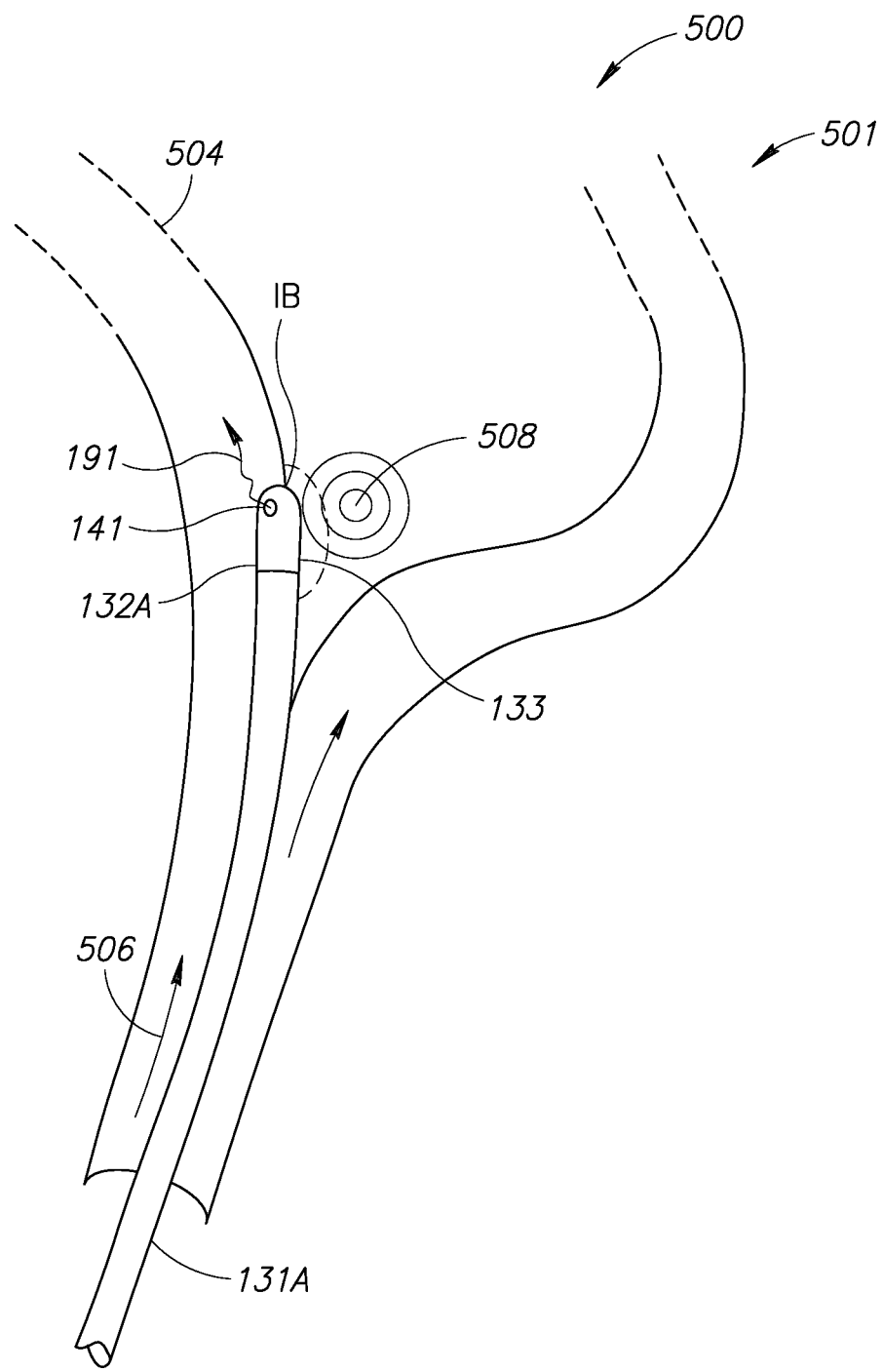
FIG. 42 shows operating the cryocatheter to generate a shallow ice ball to slightly freeze the arterial wall for anchoring the cryocatheter tip to the investigation location.

FIG. 42 shows operating the cryocatheter 130A to cool the catheter tip 132A to a temperature range of about −10° C. to −20° C. for a relatively short time duration of 1 to 2 minutes to generate a shallow ice ball IB to slightly freeze the arterial wall 504. The cryocatheter 130A generates a shallow ice ball IB of about 0.5 to 1.0 millimeter depth into the arterial wall 504 and anchors the cryocatheter tip 132 at the investigation location 511. The imaging system 192 can be employed for ensuring the catheter tip 132A is placed at the investigation location 511 and is stable.

Figure 43:
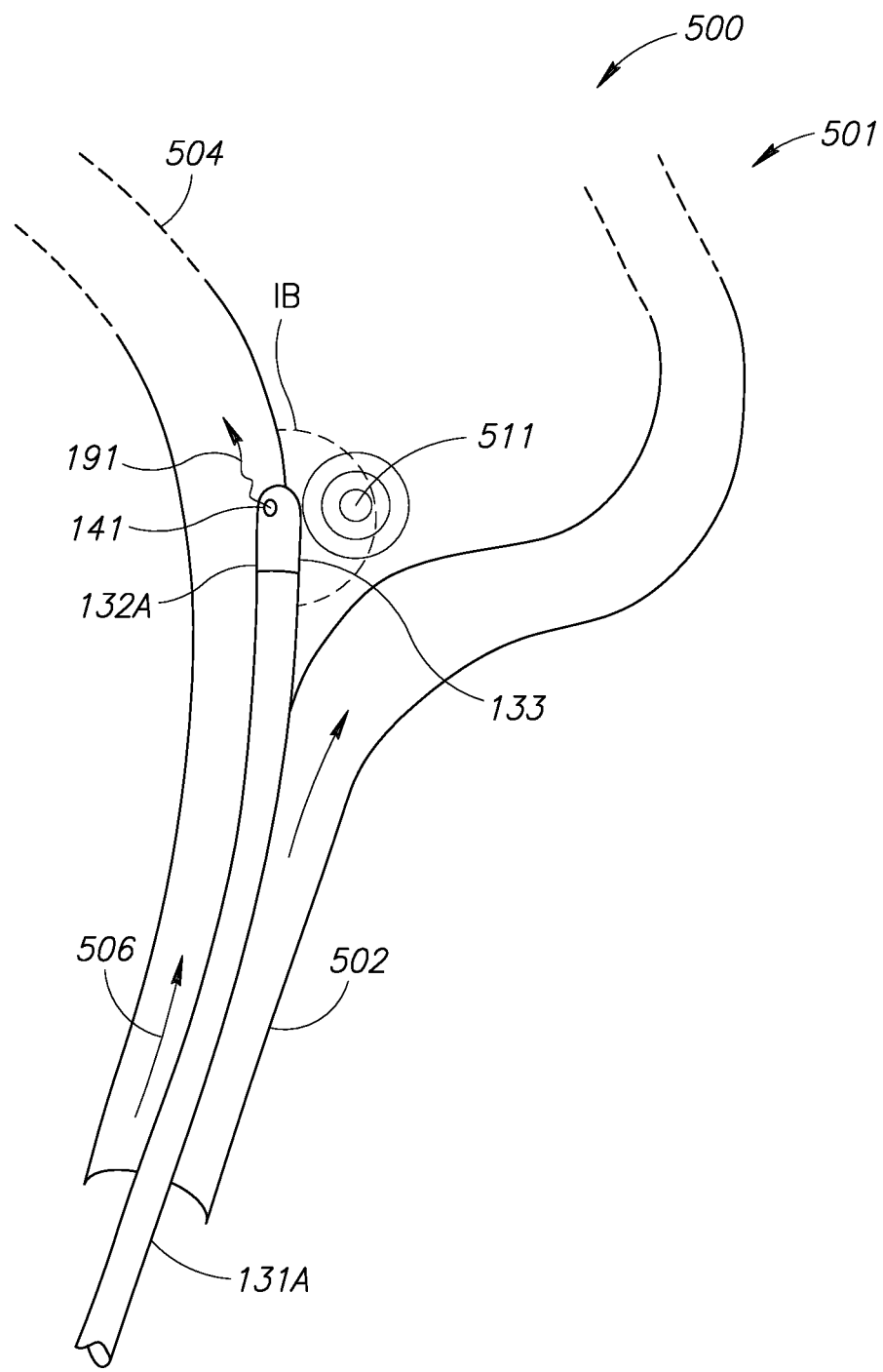
FIG. 43 shows operating the cryocatheter to generate a deep ice ball to deep freeze the arterial wall to stop electrical activity in the frozen zone.

FIG. 43 shows operating the cryocatheter system 100 to cool the catheter tip 132 to a cryotemperature from −10° C. to −30° C. and preferably in the range of −25° C. to −30° C. for a time duration from between 20 minutes to 120 minutes to generate a deep ice ball IB with a typical radius of about 3-4 millimeter to deep freeze the arterial wall 504 to stop electrical activity in the frozen region.

Figure 44:
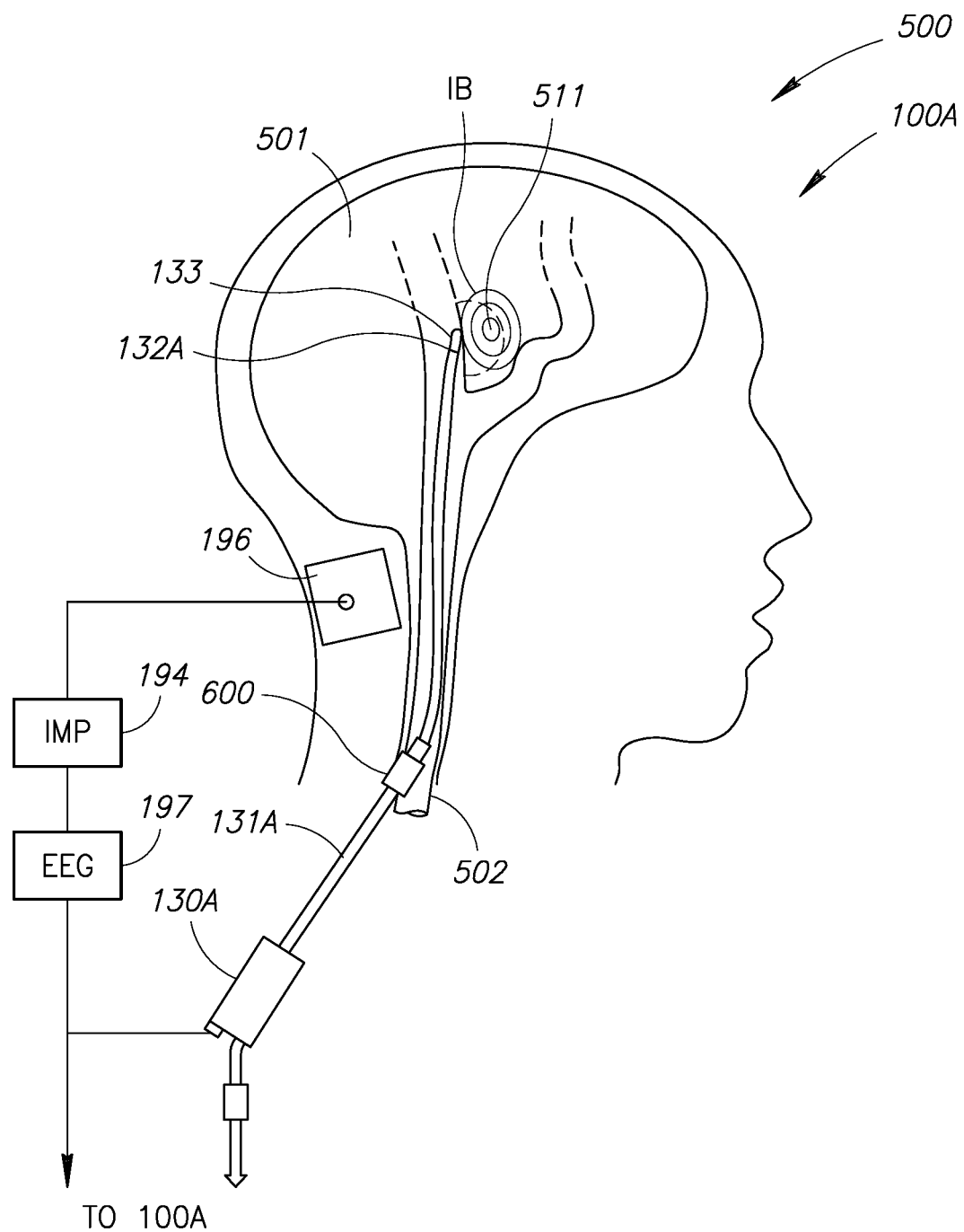
FIG. 44 shows measuring EEG signal to determine if an electrical disorder signal disappears.

FIG. 44 shows using the EEG measurement device 197 pursuant to generation of the deep ice ball IB for measuring an EEG signal for comparison to the reference EEG signal. If the electrical disorder signal in the reference EEG signal remains in the EEG signal after deep ice ball generation, then this is indicative that the investigation location is not the source of the electrical disorder signal in the reference EEG signal. Conversely, if the electrical disorder signal in the reference EEG signal does not remains in the EEG signal after deep ice ball generation, then this is indicative that the investigation location is the source of the electrical disorder signal.

Figure 45:
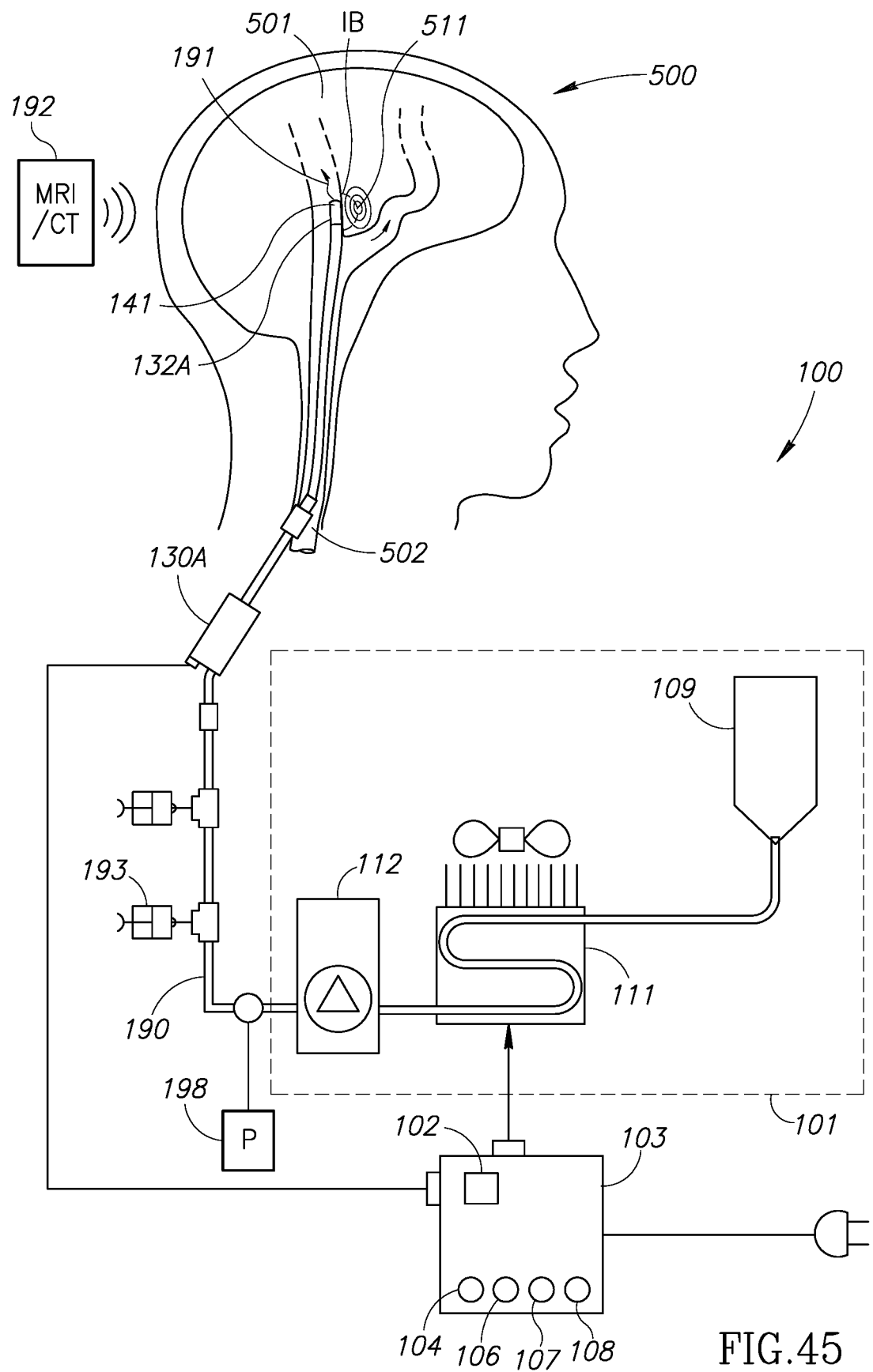
FIG. 45 shows monitoring blood flow in a treated artery to verify it is not being blocked by ice.

FIG. 45 shows monitoring the arterial blood flow 506 in the cerebral artery 503 to verify it is not being blocked by the ice ball IB formed in the arterial wall 504. Monitoring of the arterial blood flow 506 can be achieved by one of two alternative monitoring modes. First, injecting contrast agent from the contrast agent syringe 193 to the irrigation tube 190 for discharge at the investigation location 511 through the irrigation holes 141 for radiology inspection using the radiology imaging system 192. And second, the pressure monitor 198 provides an indication for artery blockage at the investigation location 511 in the case of an increase in back pressure in the irrigation tube 190.

Figure 46:
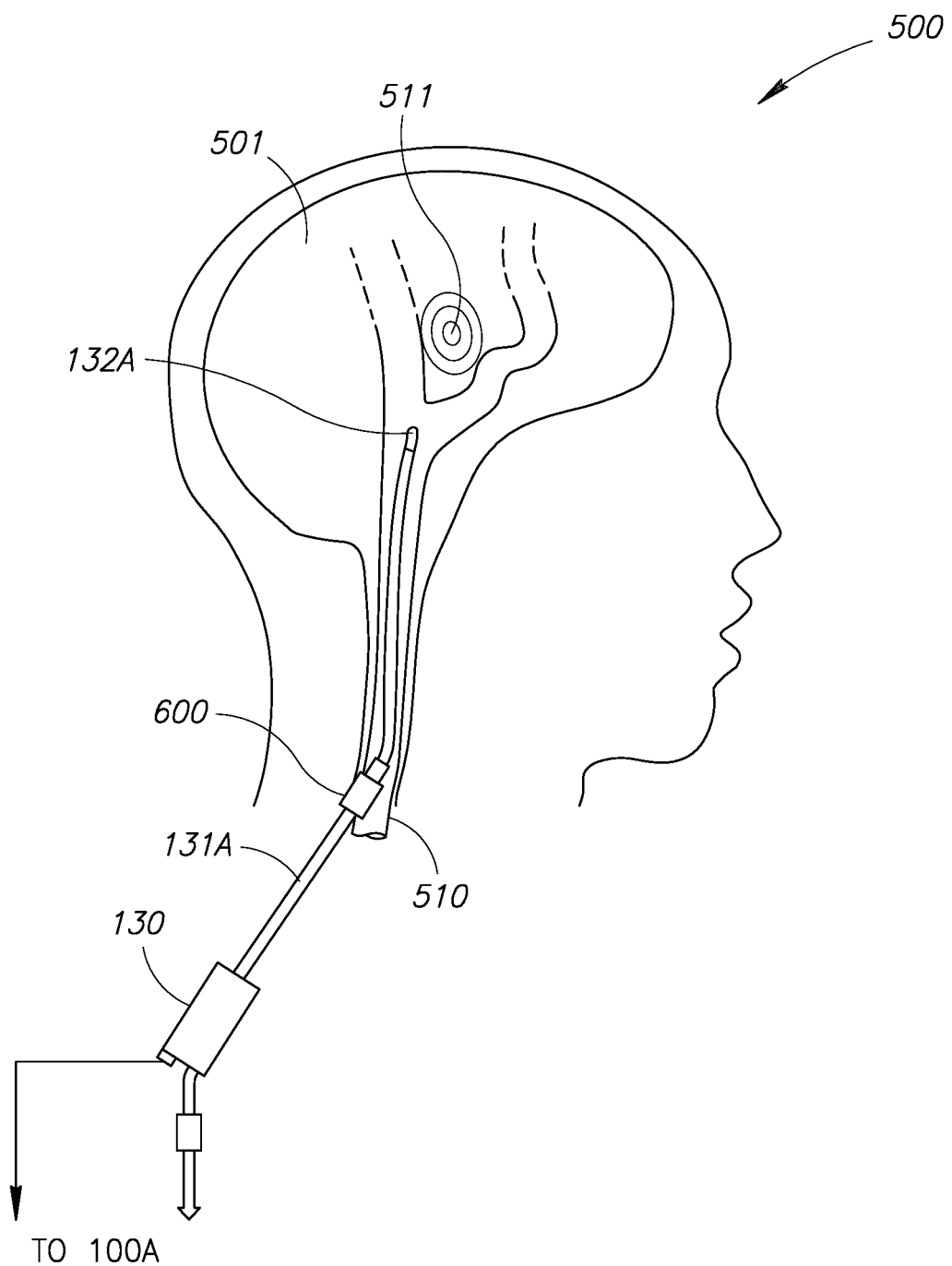
FIG. 46 shows defrosting the investigation location to release the anchoring of the cryocatheter tip.

FIG. 46 shows defrosting the investigation location 511 by operating the controller 103's DEFROST control 107 for defrosting the catheter tip 132A until the temperature of the external surface 133 of the catheter tip 132 reaches a value of about +10° C. After release the anchoring of the cryocatheter tip 132, it can be pulled back along its insertion path and withdrawn from the sheath 600. Alternatively, the cryocatheter 130A can be deployed at another investigation location.

While the invention has been described with respect to a limited number of embodiments, it will be appreciated that many variations, modifications, and other applications of the invention can be made within the scope of the appended claims.

The invention claimed is:

1. A catheter for use in a catheter system including an external coolant fluid source for delivering a downstream coolant fluid flow, the catheter comprising:
   (a) an elongated flexible catheter member having a short rigid catheter tip for introduction to a therapy site;
   (b) at least one thermoelectric module having a thermoelectric module hot side and a thermoelectric module cold side, said thermoelectric module cold side being in highly conductive thermal contact with a highly thermal conductive exterior surface of said catheter tip;
   (c) a coolant fluid supply line in flow connection with the external coolant fluid source for delivering the downstream coolant fluid flow to said catheter tip; and
   (d) a heat exchange arrangement at said catheter tip for receiving the incoming downstream coolant fluid flow from said coolant fluid supply line for cooling said thermoelectric module hot side and delivering an outgoing coolant fluid flow,
   said heat exchange arrangement having a heat transfer coefficient h and a heat exchange area Ah and capable of developing a convection temperature difference $\Delta t1$ between the downstream coolant fluid flow passing therethrough and said thermoelectric module hot side in accordance with the relationship $$\Delta t1 = \frac{Q}{h \times Ah}$$

where Q is a total thermal energy required to undergo heat transfer from said thermoelectric module hot side to said coolant fluid flow, wherein said heat exchange arrangement includes a jet impingement module including at least one jet nozzle for impinging a coolant fluid jet on an impingement surface in thermal contact with said thermoelectric module hot side for heat transfer therefrom, and wherein the at least one jet nozzle has an internal jet nozzle diameter D and an impingement height H from said impingement surface for defining a ratio D/H in the range of from about 0.5 to about 1.5.

2. The catheter according to claim 1 for cooling a trailing section of said catheter tip instead of its leading catheter dome.

3. The catheter according to claim 1 wherein said at least one thermoelectric module includes a lengthwise thermoelectric module and a widthwise thermoelectric module.

4. The catheter according to claim 1 wherein said catheter tip includes a radiofrequency (RF) electrode for ablation purposes.

5. The catheter according to claim 1 wherein said catheter tip includes an acquisition device for acquiring patient information at the therapy site.

6. The catheter according to claim 1 wherein said catheter member includes at least one vacant lumen for introduction of a surgical tool to the therapy site.

7. A catheter system comprising the catheter according to claim 1 and the external coolant fluid source.

\* \* \* \* \*